US010792268B2

(12) United States Patent
D'Agostino et al.

(10) Patent No.: US 10,792,268 B2
(45) Date of Patent: Oct. 6, 2020

(54) METHODS OF SUSTAINING DIETARY KETOSIS AND ITS EFFECTS ON LIPID PROFILE

(71) Applicant: University of South Florida, Tampa, FL (US)

(72) Inventors: Dominic Paul D'Agostino, Tampa, FL (US); Shannon Kesl, Long Beach, CA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/451,891

(22) Filed: Mar. 7, 2017

(65) Prior Publication Data

US 2017/0172969 A1 Jun. 22, 2017

Related U.S. Application Data

(63) Continuation of application No. 15/206,673, filed on Jul. 11, 2016, now abandoned, which is a
(Continued)

(51) Int. Cl.
  *A61K 31/225* (2006.01)
  *C07C 69/34* (2006.01)
  (Continued)

(52) U.S. Cl.
  CPC .......... *A61K 31/225* (2013.01); *A61K 31/22* (2013.01); *C07C 31/207* (2013.01); *C07C 69/16* (2013.01); *C07C 69/34* (2013.01); *C07B 2200/07* (2013.01)

(58) Field of Classification Search
  CPC .... A61K 31/225; A61K 31/22; C07C 31/207; C07C 69/16
  (Continued)

(56) References Cited

U.S. PATENT DOCUMENTS

| 5,126,373 A * | 6/1992 | Brunengraber ...... A61K 31/045 |
| | | 514/546 |
| 2006/0280721 A1* | 12/2006 | Veech ..................... C07C 51/09 |
| | | 424/78.37 |

(Continued)

FOREIGN PATENT DOCUMENTS

| WO | 2006118665 A2 | 11/2006 |
| WO | 2010021766 A1 | 2/2010 |
| WO | 2012154837 A2 | 11/2012 |

OTHER PUBLICATIONS

U.S. Appl. No. 15/206,673, filed Jul. 2016, D'Agostino.*

(Continued)

*Primary Examiner* — Craig D Ricci
*Assistant Examiner* — Janet L. Coppins
(74) *Attorney, Agent, or Firm* — Meunier Carlin & Curfman LLP

(57) ABSTRACT

The ketogenic diet (KD) has therapeutic implications in many disease states. It was hypothesized ketone precursor supplementation would elevate blood ketone levels to therapeutic ranges (2-7 mM) without need for dietary restriction. The effects of ketogenic agents were tested on blood glucose, ketones, and lipids with a 28-day dose escalation study in male Sprague-Dawley rats: R,S-1,3-Butandiol (BD), acetoacetate ketone ester (KE), and control ($H_2O$) (n≥8). Days 1-28, rats received a daily 5 g/kg intragastric gavage, based on previous toxicology studies. Once weekly, whole blood samples (10 μl) were acquired for analysis of glucose and βHB at 0, 0.5, 1, 4, 8, and 12 hours after test substance administration, or until βHB returned to baseline. At day 1 and 28, 10 μL of whole blood were collected to measure triglycerides, total cholesterol, and HDL concentration. Significant elevation of blood ketone was observed with a significant inverse relationship with blood glucose for the duration of the experiment. There were no significant
(Continued)

changes in the lipid panel for any of the substances. There were significant reductions in body weight when animals were treated with either BD or KE as compared to control.

9 Claims, 19 Drawing Sheets

Related U.S. Application Data continuation of application No. PCT/US2015/011165, filed on Jan. 13, 2015.

(60) Provisional application No. 61/926,635, filed on Jan. 13, 2014.

(51) Int. Cl.
  *C07C 69/16* (2006.01)
  *C07C 31/20* (2006.01)
  *A61K 31/22* (2006.01)

(58) Field of Classification Search
  USPC .......................................................... 514/547
  See application file for complete search history.

(56) References Cited

U.S. PATENT DOCUMENTS

| | | |
|---|---|---|
| 2010/0041751 A1 | 2/2010 | Henderson |
| 2017/0020844 A1 | 1/2017 | Galinski |

OTHER PUBLICATIONS

STN Registry Listing (2017), RN 107-88-0.*
Kashiwaya et al, J. Biol. Chem. (2010), vol. 285(34), pp. 25950-25956. (Year: 2010).*
Johnstone et al, Am J Clin Nutr (2008), vol. 87, pp. 44-55. (Year: 2008).*
Puchowicz et al, J. Nutri. Biochem (2000), vol. 11, pp. 281-287. (Year: 2000).*
Extended European Search Report pursuant to Rule 62 EPC (EPO Form 1507S) issued by the European Patent Office dated Apr. 26, 2017 for corresponding European Patent Application No. 15776261.8.
Bough & Rho, Anticonvulsant mechanisms of the ketogenic diet. Epilepsia 48: 43-58, 2007.
Cahill, Jr., Fuel metabolism in starvation. Annu Rev Nutr 26: 1-22, 2006.
Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.
Clarke, et al., Oral 28-day and developmental toxicity studies of (R)-3-hydroxybutyl (R)-3-hydroxybutyrate. Regul Toxicol Pharmacol. Jul. 2012;63(2):196-208.
D'Agostino, et al., Therapeutic ketosis with ketone ester delays central nervous system oxygen toxicity seizures in rats. Am J Physiol Regul Integr Comp Physiol. May 15, 2013;304(10):R829-36.
Henderson, Ketone bodies as a therapeutic for Alzheimer's disease. Neurotherapeutics 5: 470-480, 2008.
Maalouf, et al., The neuroprotective properties of calorie restriction, the ketogenic diet, and ketone bodies. Brain Res Rev. Mar. 2009;59(2):293-315.
Prins, Cerebral metabolic adaptation and ketone metabolism after brain injury. J Cereb Blood Flow Metab. Jan. 2008; 28(1): 1-16.
Veech, et al., Ketone bodies, potential therapeutic uses. IUBMB Life. Apr. 2001;51(4):241-247.
Veech, The therapeutic implications of ketone bodies: the effects of ketone bodies in pathological conditions: ketosis, ketogenic diet, redox states, insulin resistance, and mitochondrial metabolism. Prostaglandins, Leukot Essent Fatty Acids. Mar. 2004;70(3):309-319.
International search report an written opinion issued by the International Searching Authority dated Sep. 11, 2015 for corresponding international patent application PCT/US2015/011165.
International preliminary report on patentability issued by the International Bureau dated Jul. 28, 2016 for corresponding international patent application PCT/US2015/011165.
Freeman & Kossoff, Ketosis and the ketogenic diet, 2010: advances in treating epilepsy and other disorders. Adv Pediatr 57: 315-329, 2010.
Klein, et al., Ketogenic diet treatment in adults with refractory epilepsy. Epilepsy Behav 19: 575-579, 2010.
McNally & Hartman, Ketone bodies in epilepsy. J Neurochem (2012) 121, 28-35.
EPO communication pursuant to Rules 161(2) and 162 EPC (Form 1226CC) issued by the European Patent Office dated Aug. 26, 2016 for corresponding European Patent Application No. 15776261.8.
Balasse, E. O. et al., Ketone Body Production and Disposal: Effects of Fasting, Diabetes, and Exercise, Diabetes/Metabolism Reviews, 1989, vol. 5, No. 3, 247-270.
Cahill Jr., G. F. President's Address Starvation, Transactions of the American and Clinical and Climatological Association, 1983; 94:1-21.
Desrochers, S. et al., Metabolism of (R,S)-1,3-butanediol acetoacetate esters, potential parenteral and enteral nutrients in conscious pigs, American Physiological Society, 1995, E660-667.
Nair, A. B. et al., A simple practice guide for dose conversion between animals and human, Journal of basic and Clinical Pharmacy, Mar.-May 2016, vol. 7, Issue 2, 27-31.
Zhou, W. et al., The calorically restricted ketogenic diet, an effective alternative therapy for malignant brain cancer, Nutrition & Metabolism, 2007, 4:5.
Riou, J. P. et al., Antiketogenic Effect of Glucose per se in Vivo in Man and in Vitro in Isolated Rat Liver Cells, Metabolism, Jul. 1986, vol. 35, No. 7, 608-613.

* cited by examiner

A.

B.

A.

B.

A.

B.

METHODS OF SUSTAINING DIETARY KETOSIS AND ITS EFFECTS ON LIPID PROFILE

CROSS-REFERENCE TO RELATED APPLICATIONS

This application is a continuation of and claims priority to U.S. patent application Ser. No. 15/206,673, with the same title, filed Jul. 11, 2016, which claims priority to International Patent Application No. PCT/US2015/011165, with the same title, filed Jan. 13, 2015, and which claims priority to U.S. Provisional Patent Application 61/926,635, with the same title, filed on Jan. 13, 2014, and claims priority to the application, the contents of which are hereby incorporated by reference.

STATEMENT OF GOVERNMENT SUPPORT

This invention was made with government support under Grant # N00014-13-1-0062 awarded by the Department of Defense, Office of Naval Research. The government has certain rights in the invention.

FIELD OF INVENTION

This invention relates to ketogenic supplements to produce elevated and sustained levels of ketone bodies in the blood. More specifically, the invention provides a ketogenic treatment to suppress hunger.

BACKGROUND OF THE INVENTION

Ketogenic diets (KDs), calorie restriction (CR), therapeutic fasting and ketogenic precursors (e.g. ketone esters) increase blood ketone levels. Ketone bodies represent alternative energy substrates for peripheral tissues and the central nervous system (CNS). The metabolism of ketone bodies is associated with anticonvulsant effects, enhanced brain metabolism, neuroprotective, muscle sparing properties and improvement in cognitive and physical performance. Science-based improvements in efficiency of cellular metabolism, managed through ketone supplementation, could have beneficial impacts on physical, cognitive health, psychological health, warfighter resilience and a long-term impact on health with respect to the common avoidable diseases such as neurodegenerative diseases, coronary disease, diabetes and cancer. Recent evidence suggests that the health benefits from CR, KD or dietary restriction maybe be due to the effect of ketones on gene expression (Shimazu, et al. Suppression of oxidative stress by β-hydroxybutyrate, an endogenous histone deacetylase inhibitor. *Science.* 2013 Jan. 11; 339(6116):211-4) and muscle sparing properties.

Under normal conditions of the standard American diet (SAD) the brain is exclusively dependent upon the metabolism of glucose to supply its metabolic energy, which is only 2% of bodyweight but 25% of total glucose consumption. It is well known that ketones can replace glucose to supply most of the brain's metabolic energy needs (>50%) during periods of limited glucose availability resulting from starvation, CR or carbohydrate restriction as in KD, (Cahill, Jr., Fuel metabolism in starvation. *Annu Rev Nutr* 26: 1-22, 2006). During periods of starvation, CR or KD, the body mobilizes free fatty acids (FFA) from adipose tissue; however, the brain is unable to derive significant energy from FFA (Cahill, Jr., Fuel metabolism in starvation. *Annu Rev Nutr* 26: 1-22, 2006). Hepatic ketogenesis converts FFAs into the water soluble ketone bodies beta-hydroxybutyrate (BHB) and acetoacetate (AcAc), and a small percentage of AcAc spontaneously decarboxylates to acetone. During prolonged starvation or KD, large quantities of ketone bodies accumulate in the blood (>3 mM) and are transported across the blood brain barrier (BBB) by monocarboxylic acid transporters (MCFA1-4) to fuel brain function, and this ketone transport is enhanced under oxidative stress or limited glucose availability (Prins, Cerebral metabolic adaptation and ketone metabolism after brain injury. *J Cereb Blood Flow Metab* 28: 1-16, 2008). The brain derives up to 75% of its energy from ketones when glucose availability is limited (Cahill, Jr., Fuel metabolism in starvation. *Annu Rev Nutr* 26: 1-22, 2006). Starvation and dietary ketosis are often confused with diabetic ketoacidosis (DKA), but this occurs only in the absence of insulin (VanItallie & Nufert, Ketones: metabolism's ugly duckling. *Nutr Rev* 61: 327-341, 2003). At least two feedback loops prevent runaway ketoacidosis from occurring, including a ketone-induced release of insulin and ketonuria (Cahill, Jr., Fuel metabolism in starvation. *Annu Rev Nutr* 26: 1-22, 2006). The metabolic adaptations associated with starvation-induced ketosis improve mitochondrial function, decrease reactive oxygen species (ROS) production, reduce inflammation and increase the activity of neurotrophic factors (Maalouf, et al., The neuroprotective properties of calorie restriction, the ketogenic diet, and ketone bodies. *Brain Res Rev* 59: 293-315, 2009). Moreover, it is known that ketones supplied as an alternative fuel are more efficient mitochondrial energy source than glucose (reviewed in Veech, 2004).

The KD mimics the metabolic state associated with starvation (i.e. therapeutic ketosis) and is efficacious in treating drug-resistant seizure disorders (Freeman & Kossoff, Ketosis and the ketogenic diet, 2010: advances in treating epilepsy and other disorders. *Adv Pediatr* 57: 315-329, 2010). This therapeutic method is well established in children and adults (Klein, et al., Ketogenic diet treatment in adults with refractory epilepsy. *Epilepsy Behav* 19: 575-579, 2010). The anticonvulsant effects of the KD correlate with an elevation of blood ketones, especially AcAc and acetone (Bough & Rho, Anticonvulsant mechanisms of the ketogenic diet. *Epilepsia* 48: 43-58, 2007; McNally & Hartman, Ketone bodies in epilepsy. *J Neurochem,* 2011). The KD requires extreme dietary carbohydrate restriction and only modestly increases blood ketones compared to levels associated with prolonged starvation (Cahill, Jr., Fuel metabolism in starvation. *Annu Rev Nutr* 26: 1-22, 2006). In addition, the unbalanced macronutrient profile of the KD is often considered unpalatable and has the potential to negatively impact lipid profile if consumed in unrestricted amounts (Freeman & Kossoff, Ketosis and the ketogenic diet, 2010: advances in treating epilepsy and other disorders. *Adv Pediatr* 57: 315-329, 2010).

The ketogenic diet has been used to treat pediatric intractable seizures since the 1920s. The diet is currently being investigated as treatment for a broad list of disease states from cardiovascular health and type II diabetes to cancer and neurological disorders such as amyotrophic lateral sclerosis (ALS) and traumatic brain injury (TBI). Elevating blood ketones to fasting levels (>5 mM) prevents death, coma and even a hypoglycemic reaction in humans administered a normally fatal dose of insulin (Aoki & Cahill, Jr., Metabolic effects of insulin, glucagon and glucose in man. Clinical application. *Endocrinology,* edited by L. DeGroot. Et al. p 1843, New York; Grune and Straten, 1997). The classical ketogenic diet consists of a strict regimen of 4 parts fat to 1 part protein with less than 25-50 g of carbohydrates per day.

During carbohydrate deprivation, glucose availability decreases causing a metabolic shift towards fatty acid beta-oxidation and the production of ketone bodies for energy homeostasis. The two most abundant and physiologically significant ketone bodies are Acetoacetate (AcAc) and β-hydroxybutyrate WHB), while the third ketone body: Acetone is produced as a byproduct that the lungs breathe off. The carbohydrate restriction is necessary for the body to produce ketone levels in the therapeutic range 2-7 mM/L.

Many individuals, especially females, experience lethargy and light-headedness, referred to by some as the "low carb flu". This uncomfortable physiological state is due glucose withdraw in the brain and to a depletion of minerals, especially sodium and potassium in the plasma. These symptoms can be attenuated or reversed with sufficient supplementation of sodium, potassium, calcium and magnesium. Supplemental administration of minerals prevents potassium depletion via the renal-adrenal aldosterone pathway. Failure to supplement for minerals can lead to muscle cramps and fatigue. The therapeutic ketosis produced by the invention provides a rapid and sustained keto-adaptation as a metabolic therapy for a wide range of metabolic disorders, neurological disorders and cancer, and provide nutritional support for therapeutic fasting and performance enhancement.

Evidence for the KD working as a novel metabolic therapy is supported by the fact that KD-induced ketosis works when even high doses of multiple antiepileptic drugs (AEDs) fail (Kim do & Rho, The ketogenic diet and epilepsy. *Curr Opin Clin Nutr Metab Care* 11: 113-120, 2008). Thus, the KD activates mechanisms other than those targeted by any specific AED, or even combinations of AEDs. The general consensus is that therapeutic ketosis shifts energy metabolism in a way that preserves CNS function and synaptic stability. Surprisingly, no commercially available AEDs attempt to mimic therapeutic ketosis conferred by the KD. However, evidence suggests that a common ketogenic precursor (MCFA oil) induces a very mild ketosis that confers anticonvulsant effects (Neal, et al., A randomized trial of classical and medium-chain triglyceride ketogenic diets in the treatment of childhood epilepsy. *Epilepsia* 50: 1109-1117, 2009) and improves mild cognitive impairment in patients (Henderson, Ketone bodies as a therapeutic for Alzheimer's disease. *Neurotherapeutics* 5: 470-480, 2008). There is also a strong rationale for using ketones for traumatic brain injury (TBI). Cellular stress, such as those occurring in TBI, causes insulin resistance in the mitochondria which blocks pyruvate dehydrogenase (PDH), effectively blocking aerobic metabolism and forcing injured cells to generate ATP via substrate level phosphorylation. This switch occurs even in the presence of adequate brain tissue $PO_2$ and substrate. Ketone bodies enter the Tricarboxylic Acid Cycle (TCA cycle) without using the rate limiting enzyme, pyruvate dehydrogenase (PDH), bypassing the restriction of cellular respiration. This ketone-induced metabolic enhancement increases the cellular phosphorylation potential, and allows aerobic metabolism to proceed, provided the individual has sustained ketosis with a supplemental ketone bodies. Since TBI outcome is most dependent on preserving brain energy metabolism, this pathway may increase resilience to TBI by bypassing PDH and overcoming impaired glucose utilization and insulin resistance in the brain following trauma or neurodegenerative process.

Performance studies in rats, mice and human subjects have shown improved motor function, endurance and cognitive function with ketone supplementation, such as ketone esters. Resilience of cardiopulmonary and neurological function under extreme environments of oxidative stress (hyperoxia) has been achieved in rats given ketone supplementation (D'Agostino, et al. Development, testing and therapeutic applications of ketone esters (KE) for CNS oxygen toxicity (CNS-OT); i.e., hyperbaric oxygen ($HBO_2$)-induced seizures. *FASEB J.* 711.10, 2012). Recent studies at Oxford (Dr. Kieran Clark's laboratory) in elite athletes (e.g., Olympic rowers) demonstrate superior performance with respect to endurance time, volume of oxygen consumed, heart rate, blood lactate levels and power output when given ketone supplementation (BHB ester). Athletes that maintain nutritional ketosis maintain lower insulin levels and can better utilize fatty acids and ketones for fuel, effectively sparing blood glucose, which optimizes and prolongs physical and mental performance. In addition to providing an alternative fuel source, elevating blood ketones increases branch chain amino acid levels (e.g. leucine) that decreases central fatigue by reducing transport of serotonin precursors across the blood brain barrier (BBB).

Though a KD is effective at raising blood ketone levels and has potential broad applications, patient compliance is low due to the restrictive nature of the diet. There is an immediate shift back to glucose utilization, meaning decrease in ketone levels, if carbohydrates are consumed over the restrictive amount. Additionally, there are concerns with the diet regarding increasing total cholesterol and triglycerides while decreasing HDL levels. This lipid profile is a key predictor of heart health: atherosclerotic lesions, fatty streaks and fibrous plaques in the aorta and coronary arteries. This is more limiting on adult treatment with the ketogenic diet. Also, elevating blood ketones with ketogenic medical foods or exogenous ketones has been largely ineffective or problematic for a variety of reasons. Ketogenic fats, like medium chain triglyceride oil (MCFA oil) are generally not well tolerated by the gastrointestinal system, and supplementation produces only low levels of ketones (<0.5 mM) (Henderson, Ketone bodies as a therapeutic for Alzheimer's disease. *Neurotherapeutics* 5: 470-480, 2008). Oral administration of BHB and AcAc in their free acid form is expensive and ineffective at producing sustained ketosis. One idea has been to buffer the free acid form of BHB with sodium salts, but this is largely ineffective at preventing seizures in animal models and causes a potentially harmful sodium overload and mineral imbalance at therapeutic levels of ketosis (Bough & Rho, Anticonvulsant mechanisms of the ketogenic diet. *Epilepsia* 48: 43-58, 2007).

Based on the broad therapeutic potential for the ketogenic diet, the need to develop an oral ketone supplement that could elevate blood ketone levels to therapeutic ranges without dietary restriction is greater than ever.

SUMMARY OF THE INVENTION

Ketone bodies are naturally produced in the body as an alternative fuel when glucose and insulin levels are low, e.g., during starvation. The body switches from glucose-fueled ATP production to breaking down fats to generate ATP. Diets that increase ketone levels have been used to manage epilepsy, and are currently being investigated as adjunct treatment for cancer (Seyfried, & Shelton, Cancer as a metabolic disease. Nutr Metab (Lond). 2010; 7:7), amyotrophic lateral sclerosis (Zhao, et al., A ketogenic diet as a potential novel therapeutic intervention in amyotrophic lateral sclerosis. BMC Neurosci. 2006 Apr. 3; 7:29), and traumatic brain injury (Prins, Cerebral metabolic adaptation and ketone metabolism after brain injury. J Cereb Blood Flow Metab. 2008 Jan. 28(1):1-16). In 2012, Clarke et al, validated the safety and efficacy of an oral administration of a monoester of βHB in both rats and humans, showing that they were able to maintain elevated blood ketones without dietary restriction with little to no adverse side effects (Clarke, et al., Kinetics, safety and tolerability of (R)-3-hydroxybutyl (R)-3-hydroxybutyrate in healthy adult subjects. Regul Toxicol Pharmacol. 2012 August; 63(3):401-8; Clarke, et al., Oral 28-day and developmental toxicity studies of (R)-3-hydroxybutyl (R)-3-hydroxybutyrate. Regul Toxicol Pharmacol. 2012 July; 63(2):196-208). This shows the potential utility of a ketone supplement that would negate the restrictive diet while allowing the same benefits.

As such, a composition is described which causes a rapid and sustained elevation of blood ketones with a single oral administration. Exploiting the metabolic and physiological advantages of sustained ketosis (e.g. keto-adaptation), which utilize ketones as an alternative fuel to potentially improve metabolic health and performance, and suppress hunger. Individuals on the SAD can expect to get peak fat oxidation from exercise between 60-65% of maximum ($VO_2$ max); higher exertion levels will then deplete glycogen stores. Keto-adapted individuals draw proportionally more substrate from fats and ketones and can shift the peak to much higher $VO_2$ levels and thus, sustain effort for an extended duration. A sustained physiological decrease in glucose and insulin are required for sustained hepatic ketogenesis, which is very difficult for most humans.

Ketone bodies, such as beta-hydroxybutyrate and acetoacetate, have been shown to increase ATP synthesis (Veech, et al., Ketone bodies, potential therapeutic uses. IUBMB Life. 2001 April; 51(4):241-247; Veech, The therapeutic implications of ketone bodies: the effects of ketone bodies in pathological conditions: ketosis, ketogenic diet, redox states, insulin resistance, and mitochondrial metabolism. Prostaglandins, Leukot Essent Fatty Acids. 2004 March; 70(3):309-319; Maalouf, et al., The neuroprotective properties of calorie restriction, the ketogenic diet, and ketone bodies. Brain Res Rev. 2009 March; 59(2):293-315) and make ATP production more efficient (Veech, et al., Ketone bodies, potential therapeutic uses. IUBMB Life. 2001 April; 51(4):241-247; Veech, The therapeutic implications of ketone bodies: the effects of ketone bodies in pathological conditions: ketosis, ketogenic diet, redox states, insulin resistance, and mitochondrial metabolism. Prostaglandins, Leukot Essent Fatty Acids. 2004 March; 70(3):309-319; Maalouf, et al., The neuroprotective properties of calorie restriction, the ketogenic diet, and ketone bodies. Brain Res Rev. 2009 March; 59(2):293-315).

Accordingly, a composition comprising at least one ketone is disclosed, where the ketone is R,S-1,3-Butandiol, R,S-1,3-butanediol acetoacetate diester, or a combination of the two ketones. The composition has been found to suppress hunger. In light of improved effects ketosis has shown on ATP generation and utilization, as discussed above, the present composition can be used in reducing weight in individuals. The ketones are optionally administered between 2 grams and 50 grams, between 5 grams and 30 grams, or between 10 grams and 20 grams. For example, the ketone compounds are optionally administered at 2 grams, 4 grams, 5 grams, 6 grams, 7 grams, 8 grams, 9 grams, 10 grams, 11 grams, 12 grams, 13 grams, 14 grams, 15 grams, 17 grams, 19 grams, 20 grams, 22 grams, 24 grams, 26 grams, 28 grams, 30 grams, 32 grams, 34 grams, 36 grams, 38 grams, 40 grams, 42 grams, 44 grams, 46 grams, 48 grams, or 50 grams. Alternatively, the ketones are administered at between 5 g/kg to 10 g/kg. Nonlimiting examples include 5 g/kg, 5.5 g/kg, 6 g/kg, 6.5 g/kg, 7 g/kg, 7.5 g/kg, 8 g/kg, 8.5 g/kg, 9 g/kg, 9.5 g/kg, or 10 g/kg.

These compositions have been found especially useful when used to produce clinical ketosis in the patient. Preferably, blood levels above 0.5 mmol/L (mild clinical ketosis) through less than 10 mmol/L are used. In specific embodiments, the target blood levels are between about 1.0 mmol/L and about 3.0 mmol/L. Administration of the compositions at about 1 g/kg/day achieves mild ketosis, whereas 10 g/kg/day achieves high levels of ketosis. As such the ketone compositions are optionally administered at about 1 g/kg/day to about 10 g/kg/day. Nonlimiting examples include 1 g/kg/day, 1.25 g/kg/day, 1.5 g/kg/day, 2 g/kg/day, 2.5 g/kg/day, 3 g/kg/day, 3.5 g/kg/day, 4 g/kg/day, 4.5 g/kg/day, 5 g/kg/day, 5.5 g/kg/day, 6 g/kg/day, 7 g/kg/day, 8 g/kg/day, 8.5 g/kg/day, 9 g/kg/day, 9.5 g/kg/day, and 10 g/kg/day.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
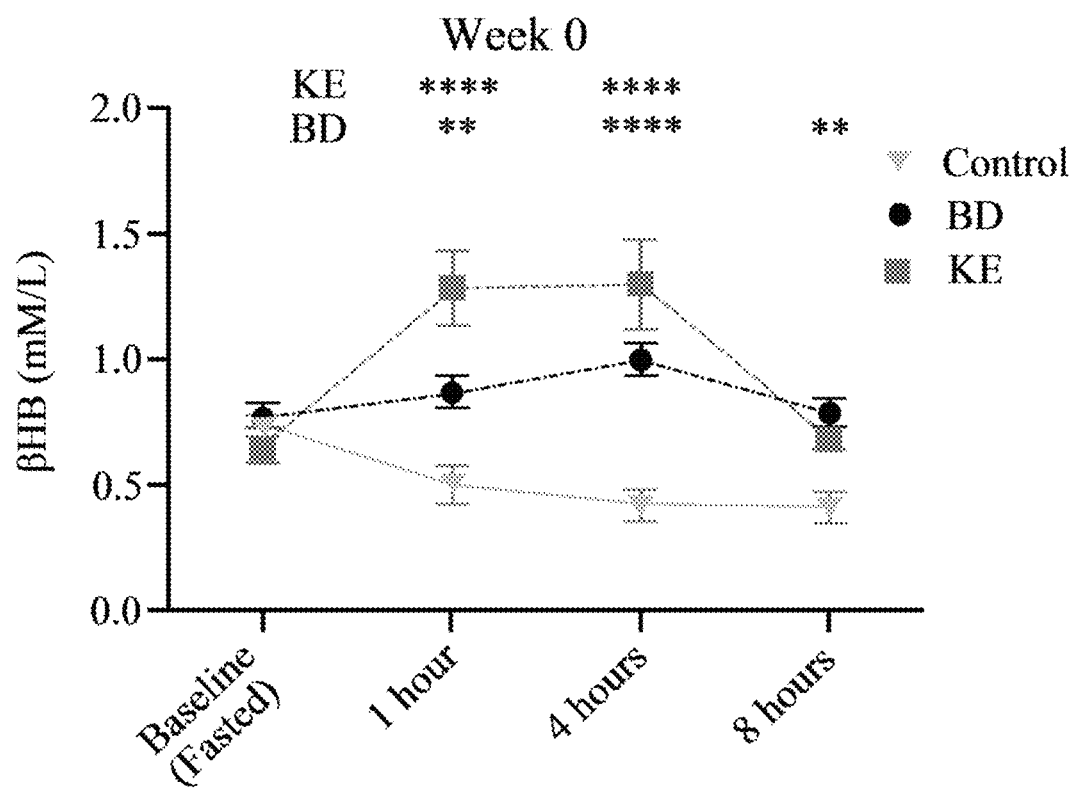
FIGS. 1(A) and (B) are graphs showing the effects of ketone supplementation on blood ketone levels. Ketone supplementation demonstrated significant elevation of ketones over 4 weeks. (A) Week 0 and (B) week 1, ketone supplements BD and KE were given at 5 g/kg for all four weeks. Both elevated ketones starting at 30 min and lasting 8 hours. Two-Way ANOVA with Dunnett's post hoc test, results considered significant if $p<0.05$. Error bars represent ±SEM. * $p<0.05$;  $p<0.01$; * $p<0.001$; **** $p<0.0001$.
Figure 1:
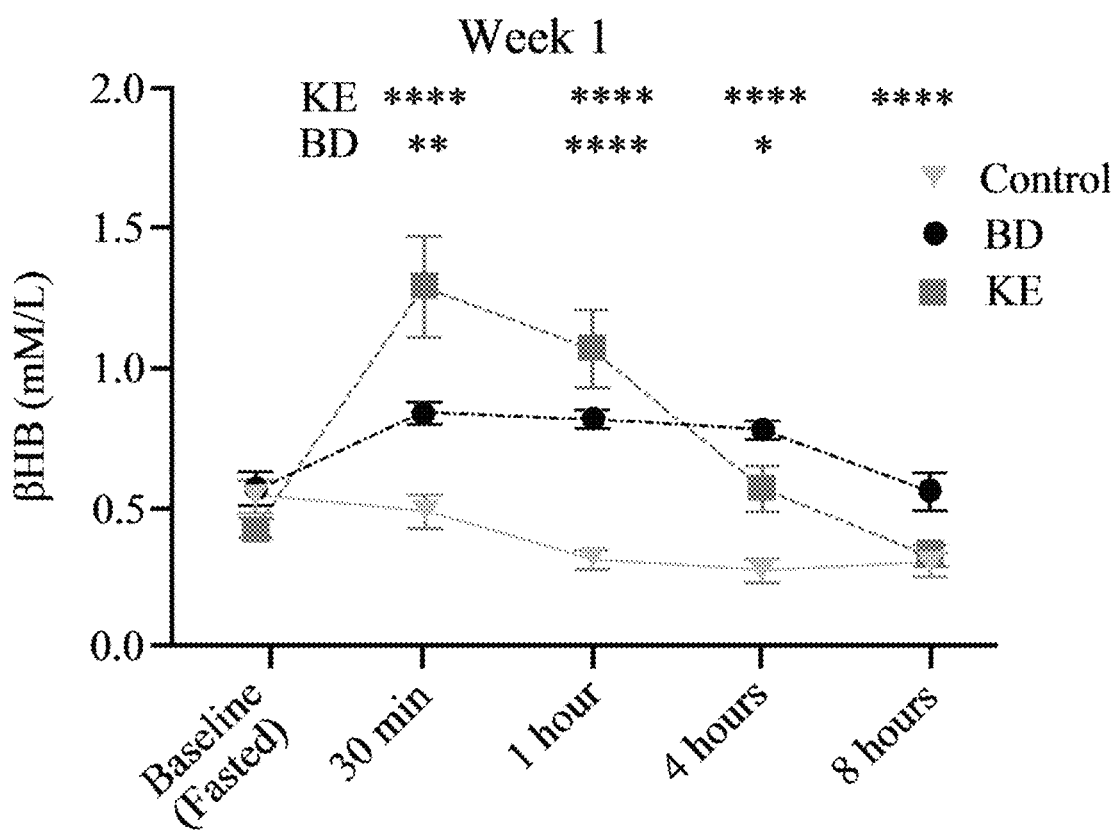
Figure 2:
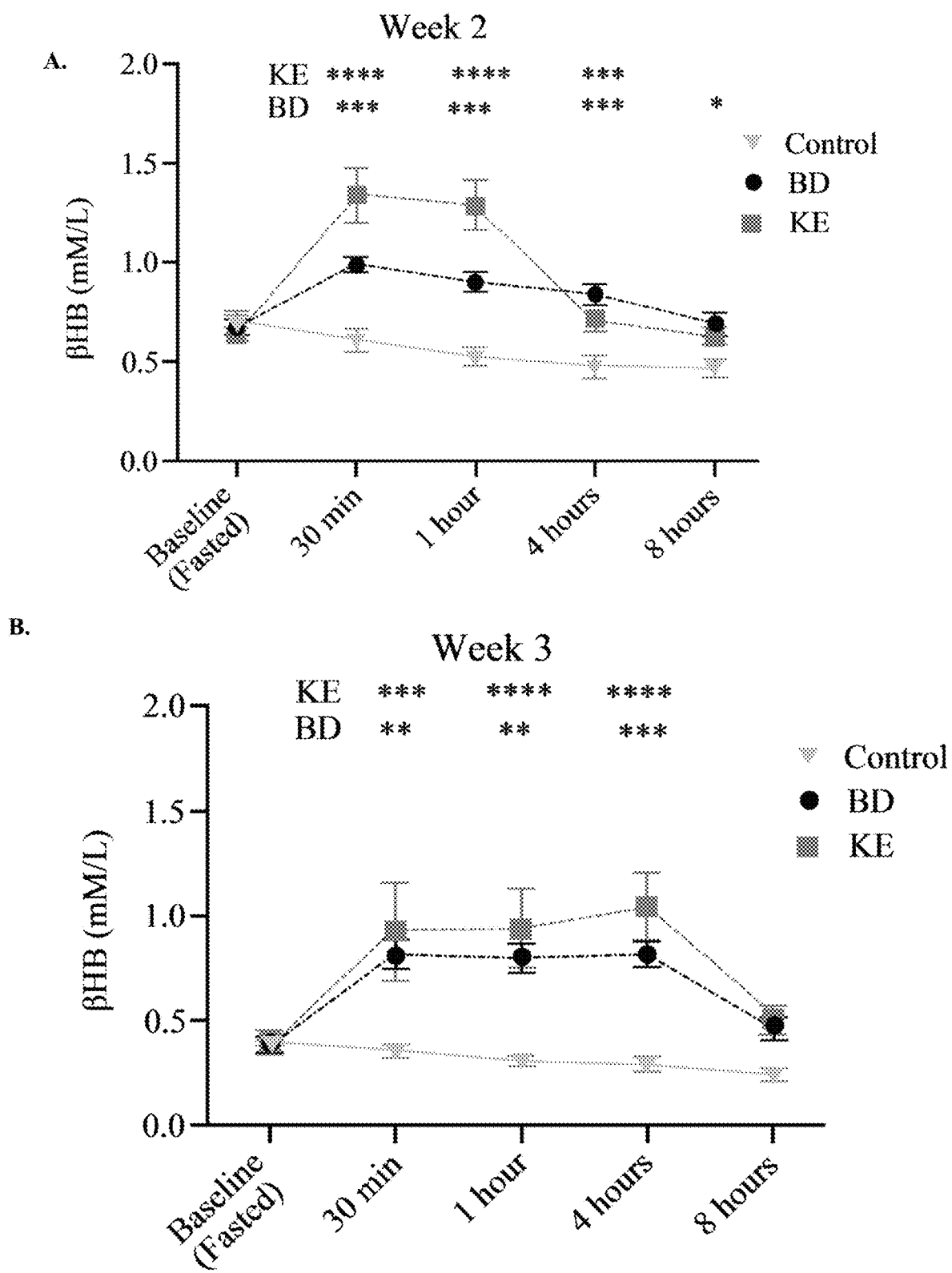
FIGS. 2(A) and (B) are graphs showing the effects of ketone supplementation on blood ketone levels. Ketone supplementation demonstrated significant elevation of ketones over 4 weeks. (A) Week 2 and (B) week 3, ketone supplements BD and KE were given at 5 g/kg for all four weeks. Both elevated ketones starting at 30 min and lasting 8 hours. Two-Way ANOVA with Dunnett's post hoc test, results considered significant if $p<0.05$. Error bars represent ±SEM. * $p<0.05$;  $p<0.01$; * $p<0.001$; **** $p<0.0001$.

As used herein, the singular forms "a," "an" and "the" include plural referents unless the context clearly dictates otherwise. Thus, for example, reference to "a ketone precursor" includes a mixture of two or more ketone precursors and the like, unless otherwise specified.

As used herein, "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. In specific embodiments, "about" means approximately or nearly and in the context of a numerical value or range set forth means ±15% of the numerical. "About" is understood to refer to numbers in a range of numerals. Moreover, all numerical ranges herein should be understood to include all integer, whole or fractions, within the range.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein As used herein "beta-hydroxybutyrate," also known as BHB or BHB, is a carboxylic acid having the general formula $CH_3CH_2OHCH_2COOH$ which may be utilized by a patient's body as a fuel source during instances of low glucose levels in the patient and is considered a ketone body. In the present invention, salt variants of beta-hydroxybutyrate are disclosed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

"Ketosis" as used herein refers to a subject having blood ketone levels >0.5 mmol/L. Ketone levels sustained above 0.5 mmol/L and ideally in the range of 1.0 to 3.0 mmol/L appear to offer the most therapeutic effects in humans. Levels of ketosis above 10.0 mmol/L are associated with signs of ketoacidosis. Ketosis may improve mitochondrial function, elevate Krebs cycle intermediates (e.g. succinate, fumarate), decrease ROS production, reduce inflammation, elevated adenosine and increase the activity of neurotrophic factors associated with enhanced wound repair.

As used herein "patient", means members of the animal kingdom, including mammals, such as but not limited to, primates including humans, gorillas and monkeys; rodents, such as mice, fish, reptiles and birds. As used herein "animal" means a multicellular, eukaryotic organism classified in the kingdom Animalia or Metazoa. The term includes, but is not limited to, mammals. Non-limiting examples include, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals. The patient may be any animal requiring therapy, treatment, or prophylaxis, or any animal suspected of requiring therapy, treatment, or prophylaxis. The term treatment, as used in this definition only, is intended to mean that regiment described is continued until the underlying tissue damage is resolved, whereas therapy requires that the regiment alleviate one or more symptoms of the underlying damage, such as formation of reactive oxygen species.

As used herein, the term "therapeutically effective amount" refers to that amount of a therapy (e.g., a ketogenic agent) sufficient to result in the amelioration of oxidation via reactive oxygen species or improving the outcome of wound healing, prevent chronic ulceration, reduce scar formation, or to enhance or improve the therapeutic effect(s) of another wound repair therapy.

The term "administration" or "administering" is used to describe the process in which individual ketone esters, including R,S-1,3-butanediol acetoacetate diester, and butanediol, R,S-1,3-butanediol, in any combination are delivered to a subject. The composition may be administered in various ways including oral, intragastric, and parenteral (referring to intravenous and intra-arterial and other appropriate parenteral routes), among others. Each of these conditions may be readily treated using other administration routes of beta-hydroxybutyrate salts in combination with medium chain triglycerides, derivatives, or any combination thereof to treat a disease or condition.

Administration will often depend upon the amount of compound administered, the number of doses, and duration of treatment. In an embodiment, multiple doses of the agent are administered. The frequency of administration of the agent can vary depending on any of a variety of factors, such as timing of treatment from previous treatments, objectives of the treatment, i.e., weight loss or treatment of cancer or neurological disease, and the like. The duration of administration of the agent, e.g., the period of time over which the agent is administered, can vary, depending on any of a variety of factors, including patient response, desired effect of treatment, etc.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

Statistics

All data are presented as the mean±standard error of the mean (SEM). All calculations were performed using statistical analysis software GraphPad PRISM™ version 6.0a. Statistical significance was defined as $p<0.05$. All data were compared to control at the applicable time points using a two-way ANOVA with Dunnet's multiple comparisons test.

Example 1

BD was purchased from Sigma (Milwaukee, Wis.). R,S-1,3-butanediol acetoacetate diester (KE) synthesized as previously described (D'Agostino, et al., Therapeutic ketosis with ketone ester delays central nervous system oxygen toxicity seizures in rats. Am J Physiol Regul Integr Comp Physiol. 2013 May 15; 304(10):R829-36). Briefly, R,S-1,3-butanediol and t-butylacetoacetate were purchased from Sigma (Milwaukee, Wis., USA). All commercial solvents and reagents used were high-purity reagent-grade materials. KEs were synthesized by transesterification of t-butylacetoacetate with R,S-1,3-butanediol (Savind Inc., Seymour, Ill.). The resultant product consisted of a mixture of monoesters and diester, the ratio of which could be adjusted by varying the stoichiometry of reactants. Following synthesis the crude product was distilled under reduced pressure to remove all solvents and starting materials, and the resultant BD-AcAc or BD-AcAc2 was obtained and assessed for purity using gas chromatography-mass spectrometry (GC-MS). The KEs synthesized, R,S-1,3-butanediol acetoacetate (BD-AcAc) and R,S-1,3-butanediol acetoacetate diester (BD-AcAc2), are non-ionized sodium-free and pH-neutral precursors of AcAc.

Adult male Sprague-Dawley rats (n=74), 275-325 grams, were obtained from Harlan, and randomly assigned to the following groups: control (water), R,S-1,3-butanediol (BD), or R,S-1,3-butanediol acetoacetate diester (KE). Rats were treated daily with 5 g/kg intragastric gavage of BD or KE for days 1-28. Animals were weighed once per week to maintain accurate dosage using the Mittler Toledo SB16001 scales. Gavage was given between 10 am-1 pm daily to eliminate variance based on regular eating patterns. Diets were not restricted for this study.

Once a week, animals were fasted, with water still available for 4 hours prior to intragastric gavage to eliminate blood glucose and ketone variance of regular eating habits. Whole blood samples (10 µl) were acquired from the saphenous vein for analysis of glucose and βHB utilizing the commercially available glucose and ketone monitoring system Precision Xtra™ (Abbott Laboratories, Abbott Park, Ill.) at time 0, 0.5, 1, 4, 8, and 12 hours after test substance administration, or until βHB returned to baseline. On Day 0 (Week 0) and Day 28 (Week 4), whole blood samples (10 µL) were acquired for analysis of total cholesterol, HDL, and triglycerides for a lipid panel utilizing the commercially available home cholesterol analyzer Cardio Chek™ (Polymer Technology Systems, Inc., Indianapolis, Ind.) at time 0.

Figure 3:
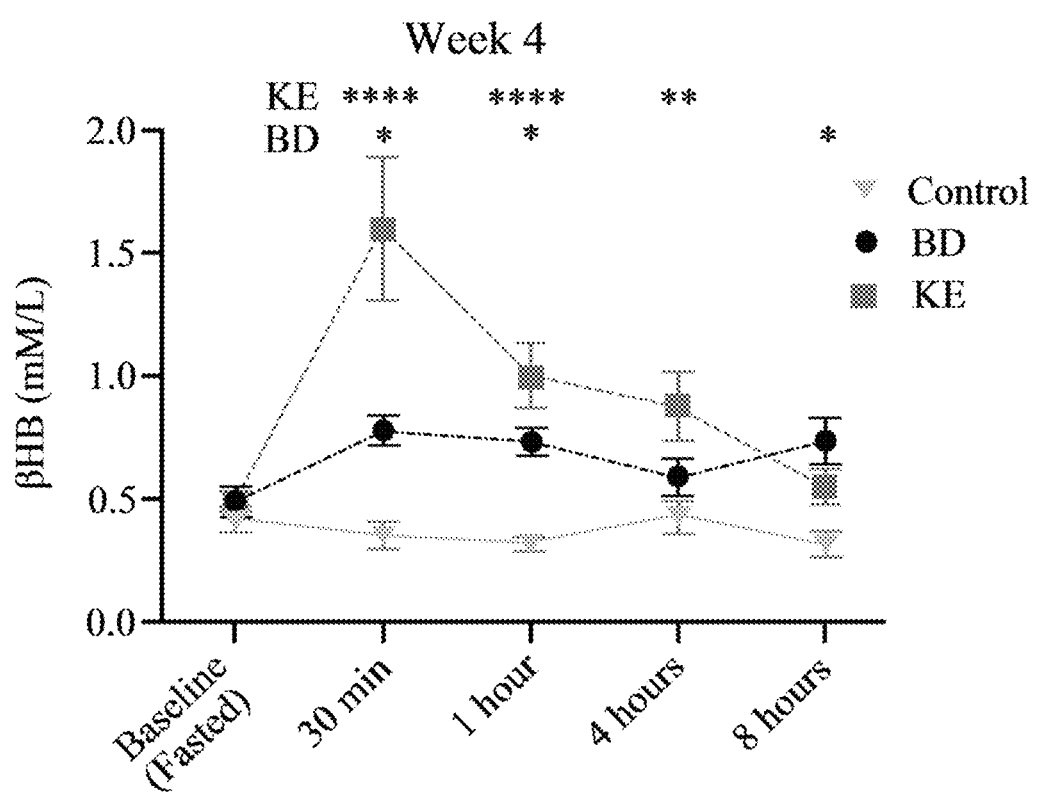
FIG. 3 is a graph showing the effects of ketone supplementation on blood ketone levels. Ketone supplementation demonstrated significant elevation of ketones over 4 weeks. Week 4, ketone supplements BD and KE were given at 5 g/kg for all four weeks. Both elevated ketones starting at 30 min and lasting 8 hours. Two-Way ANOVA with Dunnett's post hoc test, results considered significant if $p<0.05$. Error bars represent ±SEM. * $p<0.05$;  $p<0.01$; * $p<0.001$; **** $p<0.0001$.

Over the 28-day experiment, administered amounts of the ketone precursors R,S-1,3-butanediol (BD) and R,S-1,3-butanediol acetoacetate diester (KE) remained constant, at 5 g/kg. BD-treated rats showed a moderate increase in ketone bodies, which tended to peak at 30 minutes and remain at constant elevated levels of around 0.8 to 1.0 mM/L through to 4 hours post-treatment, as seen in FIGS. 1(A) through 3. Slight deviations are apparent, as seen in FIG. 1(A), which showed a peak of 1.0 mM/L at 4 hours, and FIG. 3, which showed an initial peak of about 0.8 mM/L at 30 minutes that began to subside, followed by a second peak of about 0.8 mM/L at 8 hours. It is possible these deviations are due to administration, as FIG. 1(A) shows treatment at week 0 and FIG. 3 shows treatment at week 6. However, these variations are likely due to artifacts, with the overall trend of a 30 minute-peak evidencing the physiological response to BD. KE-treated rats showed an increase in ketone bodies 30 minutes after administration to about 1.3 to 1.5 mM/L, which then slowly decreased over the 8 hour-testing window. Similar to BD treatment, the KE results did show deviations from the overall trend. In FIG. 1(A), ketone levels remained elevated through 4 hours before decreasing, and in FIG. 2(B), ketone levels plateaued at 30 minutes, followed by an increase to a peak level at 4 hours of about 1.1 to 1.2 mM/L. In light of the variations, it appears the deviations are due to sampling differences, and that the physiological response is reflected by the overall trends, which show significant elevations in BHB levels until 8 hours post-treatment.

Figure 4:
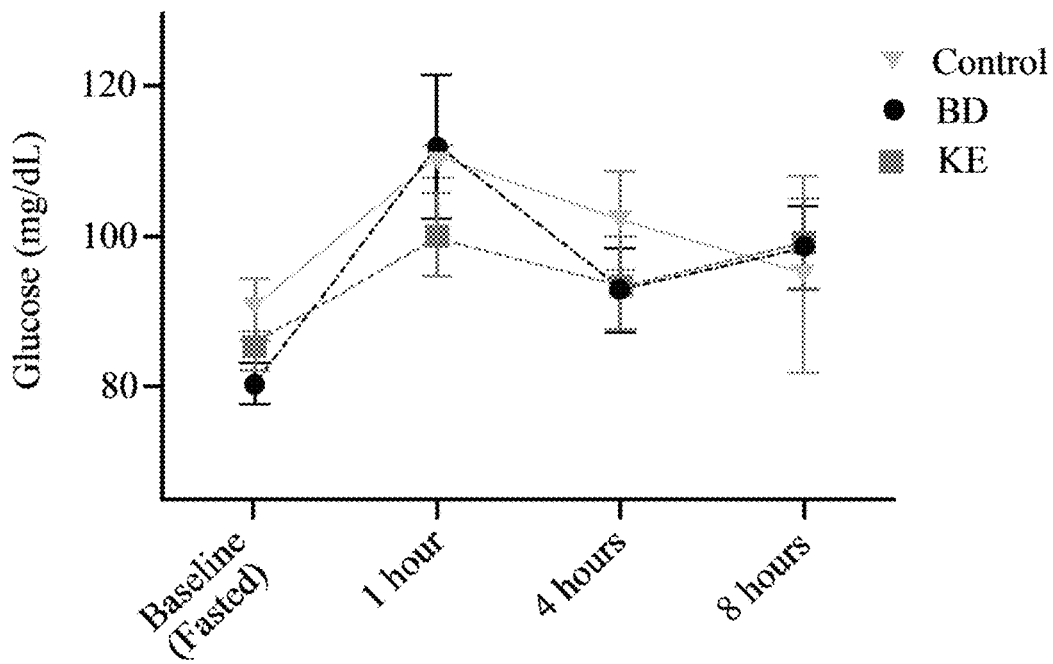
FIGS. 4(A) and (B) are graphs showing the effects of ketone supplementation on blood glucose levels at (A) week 0 and (B) week 1. Two-Way ANOVA with Dunnett's post hoc test, results considered significant if $p<0.05$. Error bars represent ±SEM.
Figure 4:
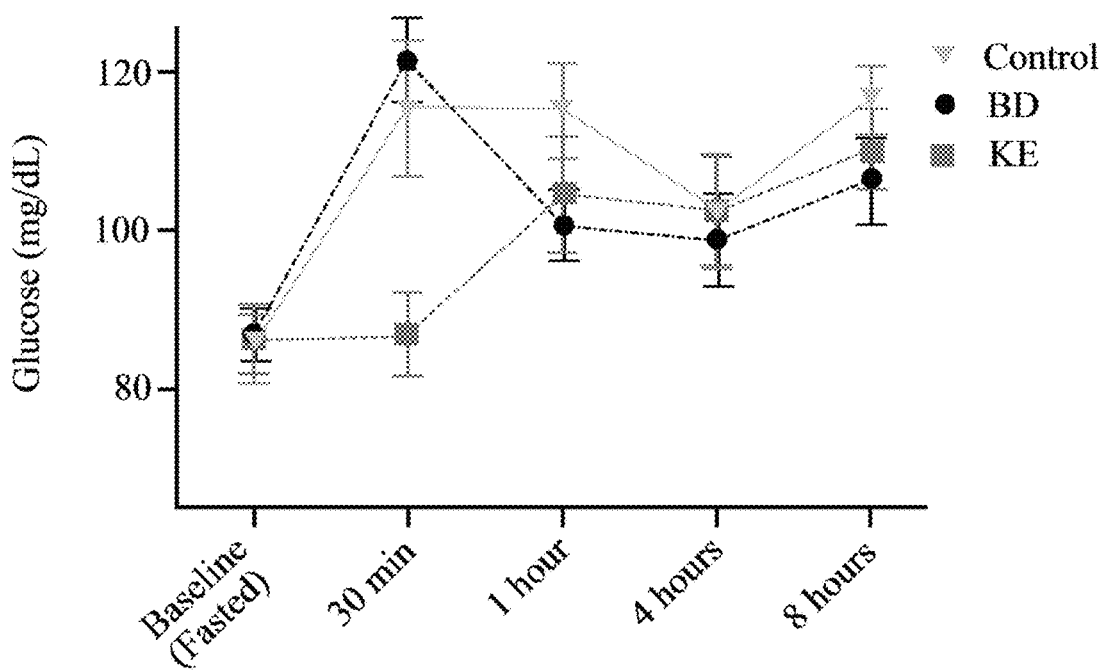
Figure 5:
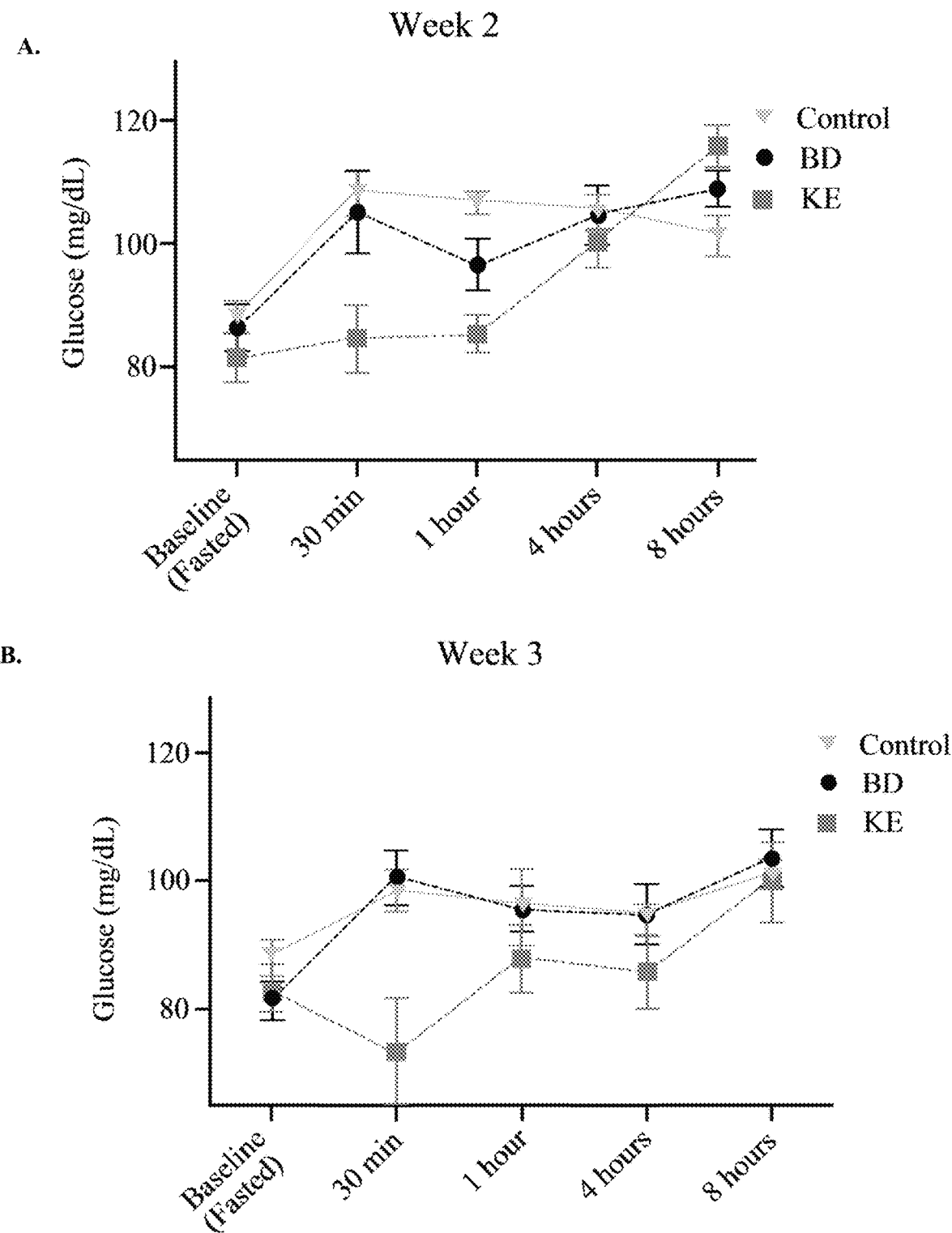
FIGS. 5(A) and (B) are graphs showing the effects of ketone supplementation on blood glucose levels at (A) week 2 and (B) week 3. Two-Way ANOVA with Dunnett's post hoc test, results considered significant if $p<0.05$. Error bars represent ±SEM.
Figure 6:
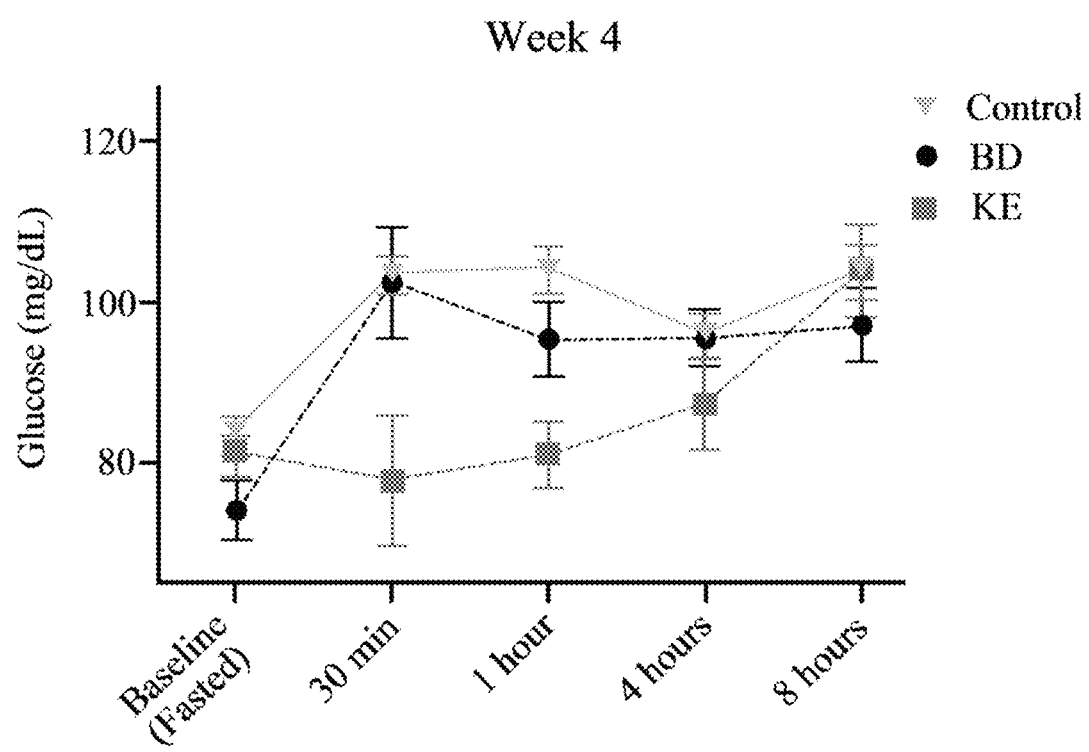
FIG. 6 is a graph showing the effects of ketone supplementation on blood glucose levels at week 4. Two-Way ANOVA with Dunnett's post hoc test, results considered significant if $p<0.05$. Error bars represent ±SEM.

Administered amounts of the ketone precursors R,S-1,3-butanediol (BD) and R,S-1,3-butanediol acetoacetate diester (KE) resulted in a rapid reduction in blood glucose. At week 0, KE treatment showed a reduction in glucose levels by 1 hour after treatment, as seen in FIG. 4(A), which continued the trend in week 1, seen in FIG. 4(B). BD showed a non-significant reduction in week 1. By week 2, KE treatment showed enhanced reduction in glucose, as levels at 1 hour after treatment were also reduced, as seen in FIG. 5(A), and showed moderate reductions at 4 hours after treatment by week 3, as seen in FIG. 5(B). By week 4, KE treatment resulted in reduced glucose levels through 4 hours after treatment, as seen in FIG. 6. BD treatment did not appear to drastically affect glucose levels. KE-treatment reductions in glucose levels began at 30 minutes after treatment through 4 hours, which was enhanced as treatment progressed through weeks 3 and 4.

Figure 7:
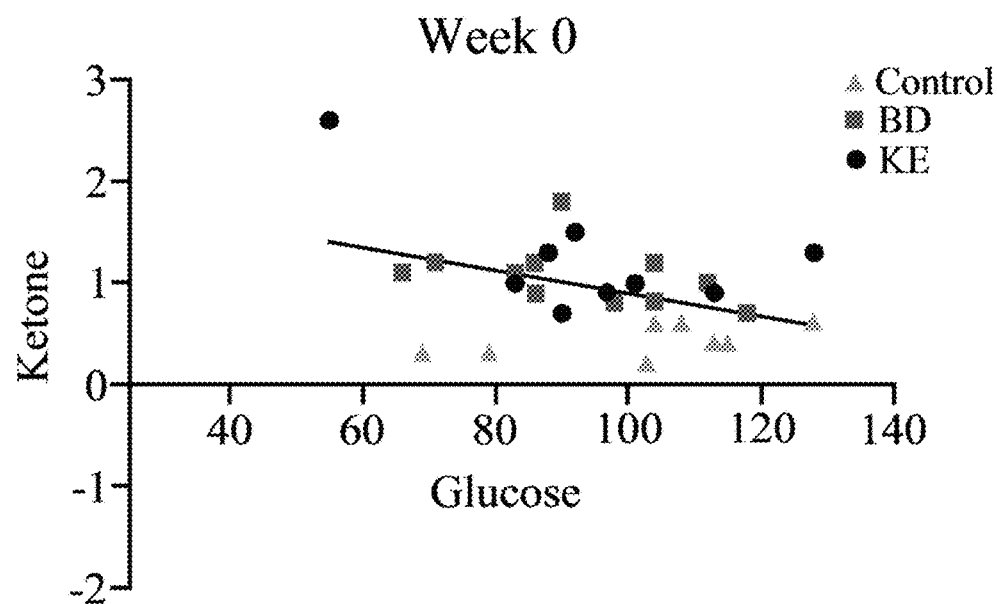
FIGS. 7(A) and (B) are graphs showing a binary regression analysis between ketone and glucose levels at (A) week 0 and (B) week 1. Linear regression analysis results were considered significant if $p<0.05$.
Figure 7:
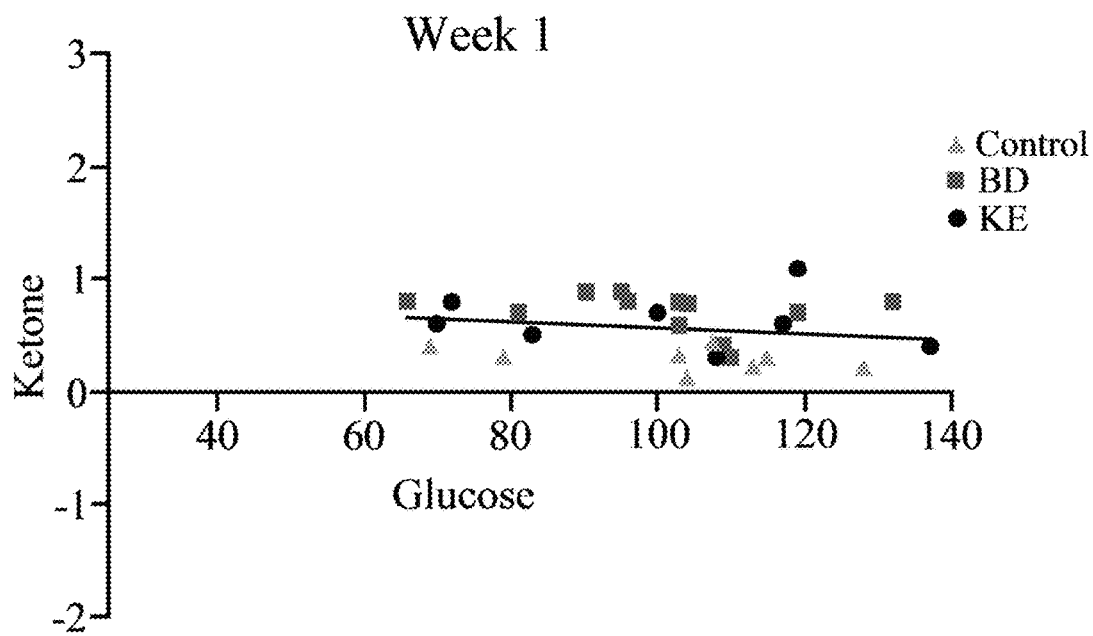
Figure 8:
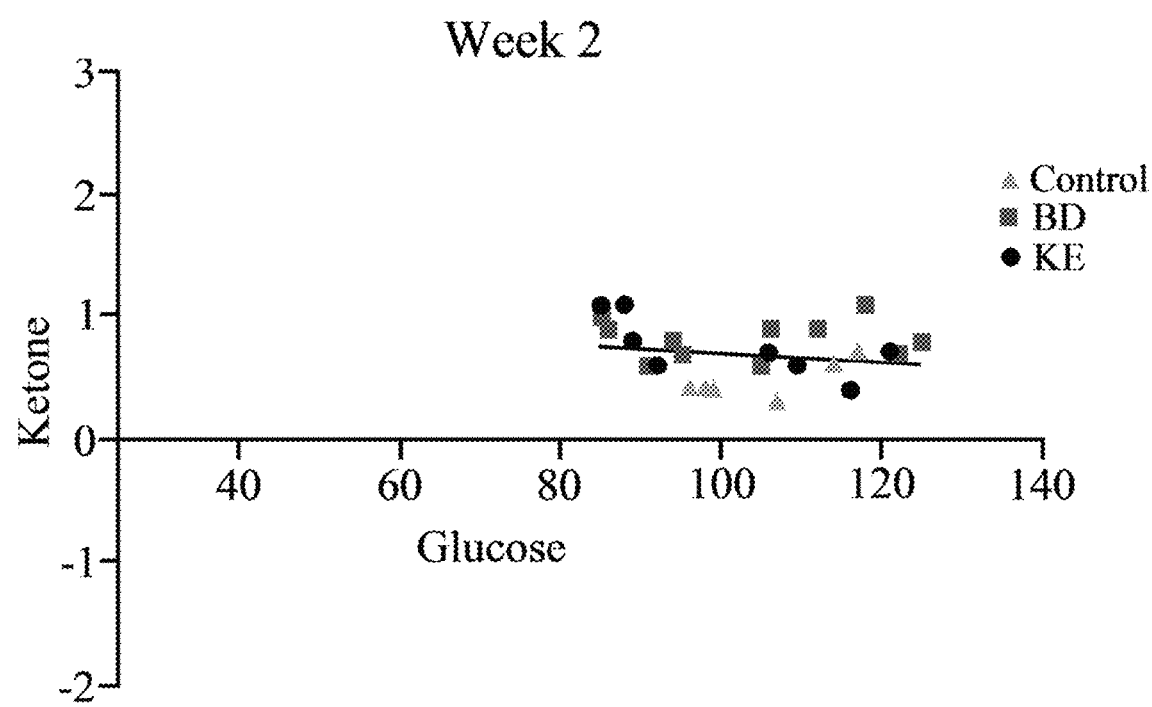
FIG. 8 is a graph showing a binary regression analysis between ketone and glucose levels at week 2. Linear regression analysis results were considered significant if p<0.05.
Figure 9:
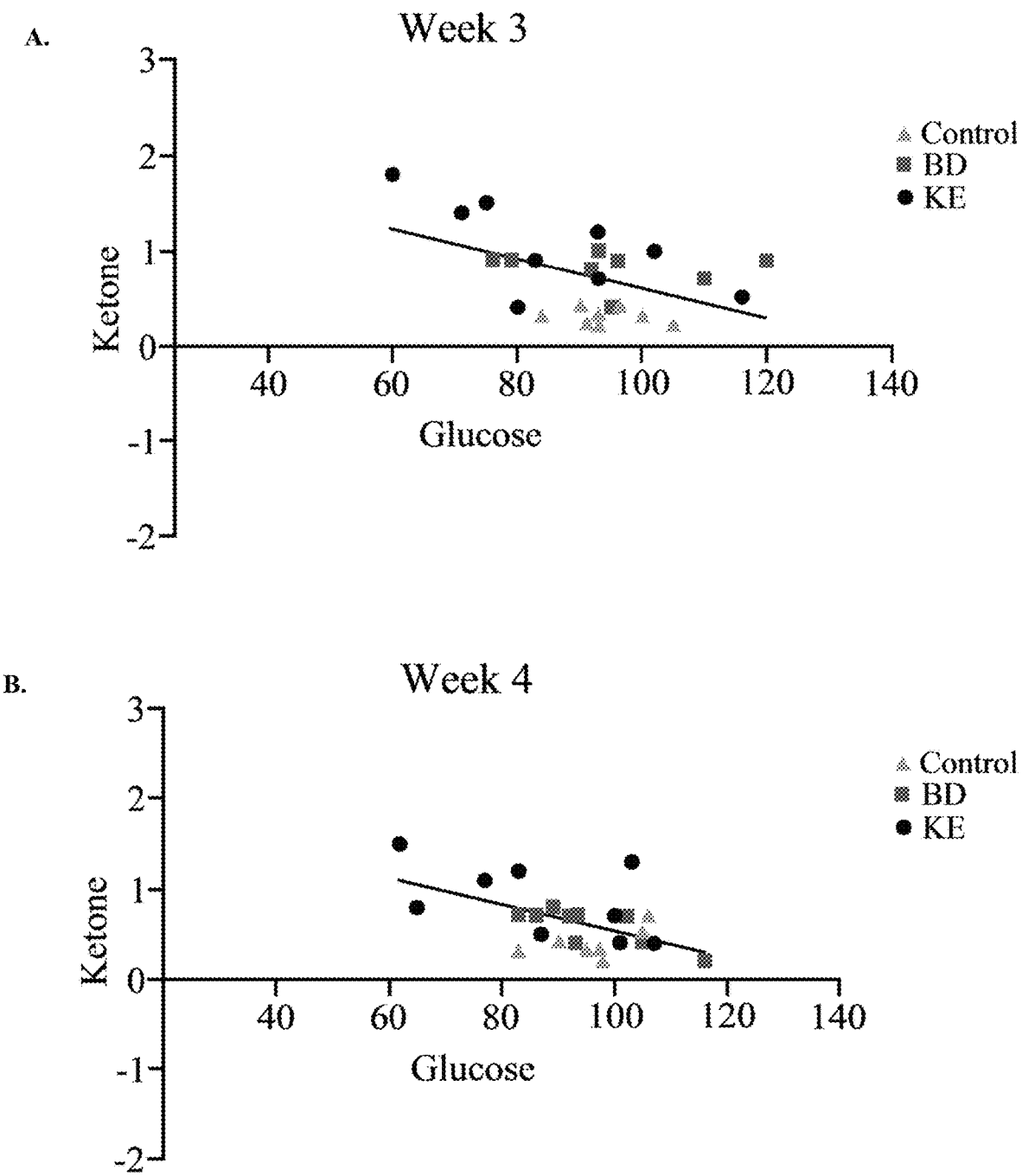
FIGS. 9(A) and (B) are graphs showing a binary regression analysis between ketone and glucose levels at (A) week 3 and (B) week 4. At week 4, BD (5 g/kg) showed a significant correlation between blood ketone levels and blood glucose levels. Linear regression analysis results were considered significant if p<0.05.

In week 0 (baseline), KE (5 g/kg) supplemented rats showed a large, but non-significant, inverse relationship between elevated blood ketone levels and decreased blood glucose levels, as seen in FIG. 7(A) and Table 1. BD (5 g/kg) supplemented rats also showed a modest, non-significant inverse relationship. By comparison, control-treated rats did not show any correlation between blood ketone levels and blood glucose levels. Weeks 2 and 3 showed less correlation between blood ketone levels and blood glucose levels, as seen in FIGS. 7(B) and 8. At week 3, KE-supplemented rats demonstrated a non-significant inverse relationship between elevated blood ketone levels and decreased blood glucose levels, seen in FIG. 9(A). However, BD-treated rats did not show a similar correlation, as seen in FIG. 9(A). At week 4, KE and BD treatment indicated an inverse relationship, though only KE treatment showed a significant correlation between blood ketone levels and blood glucose levels, as seen in FIG. 9(B) and Table 1.

Figure 10:
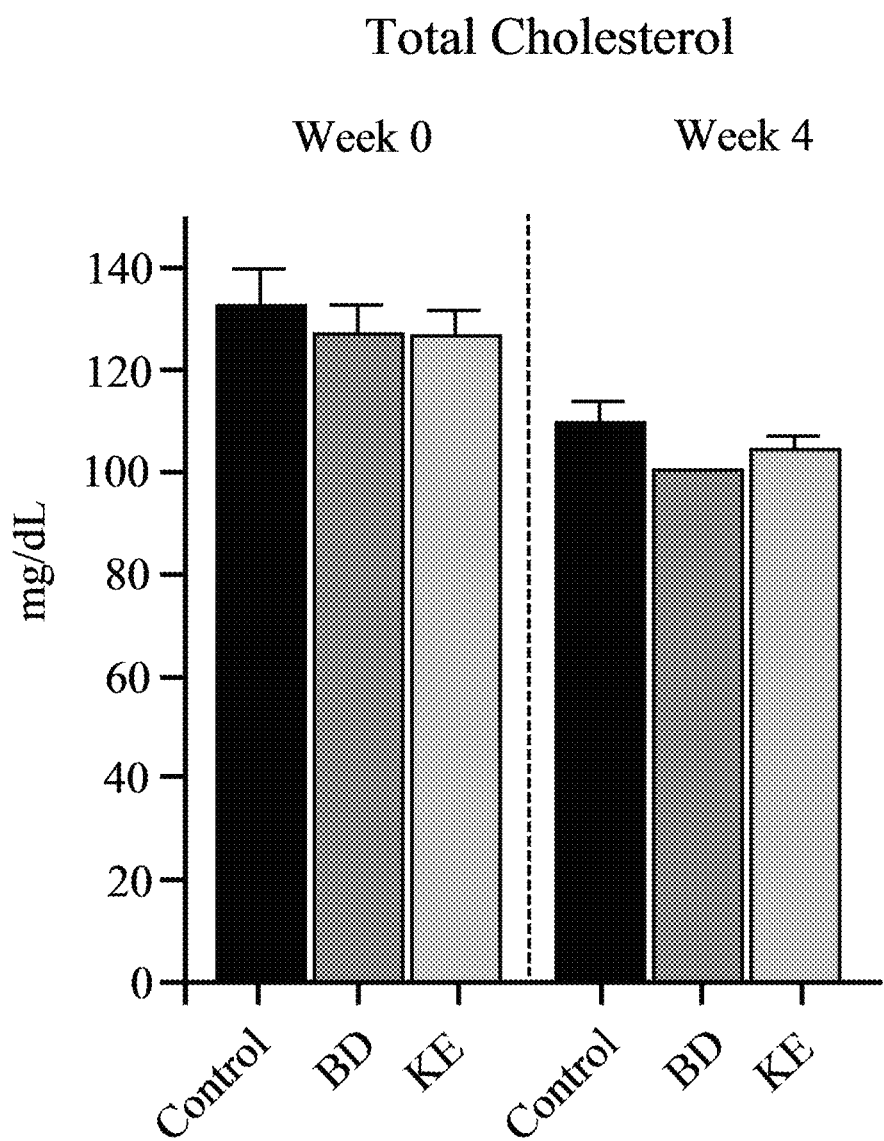
FIG. 10 is a graph showing ketone supplementation does not affect lipid profile. At week 0 and week 4 total cholesterol were not significantly different from control in any of the test substances. Two-Way ANOVA with Dunnett's post hoc test, results considered significant if p<0.05. Error bars represent ±SEM.
Figure 11:
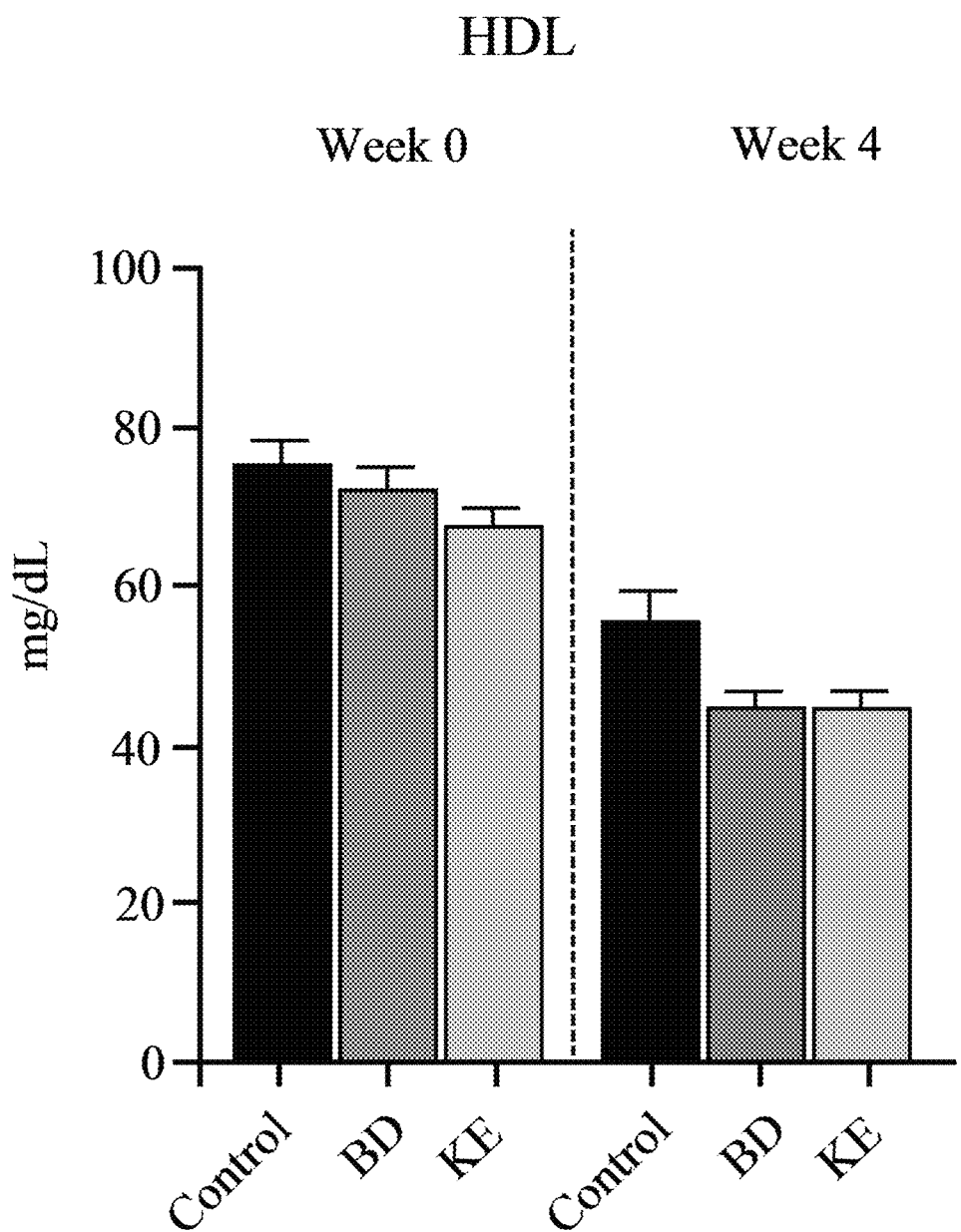
FIG. 11 is a graph showing ketone supplementation does not affect lipid profile. At week 0 and week 4 HDL were not significantly different from control in any of the test substances. Two-Way ANOVA with Dunnett's post hoc test, results considered significant if p<0.05. Error bars represent ±SEM.
Figure 12:
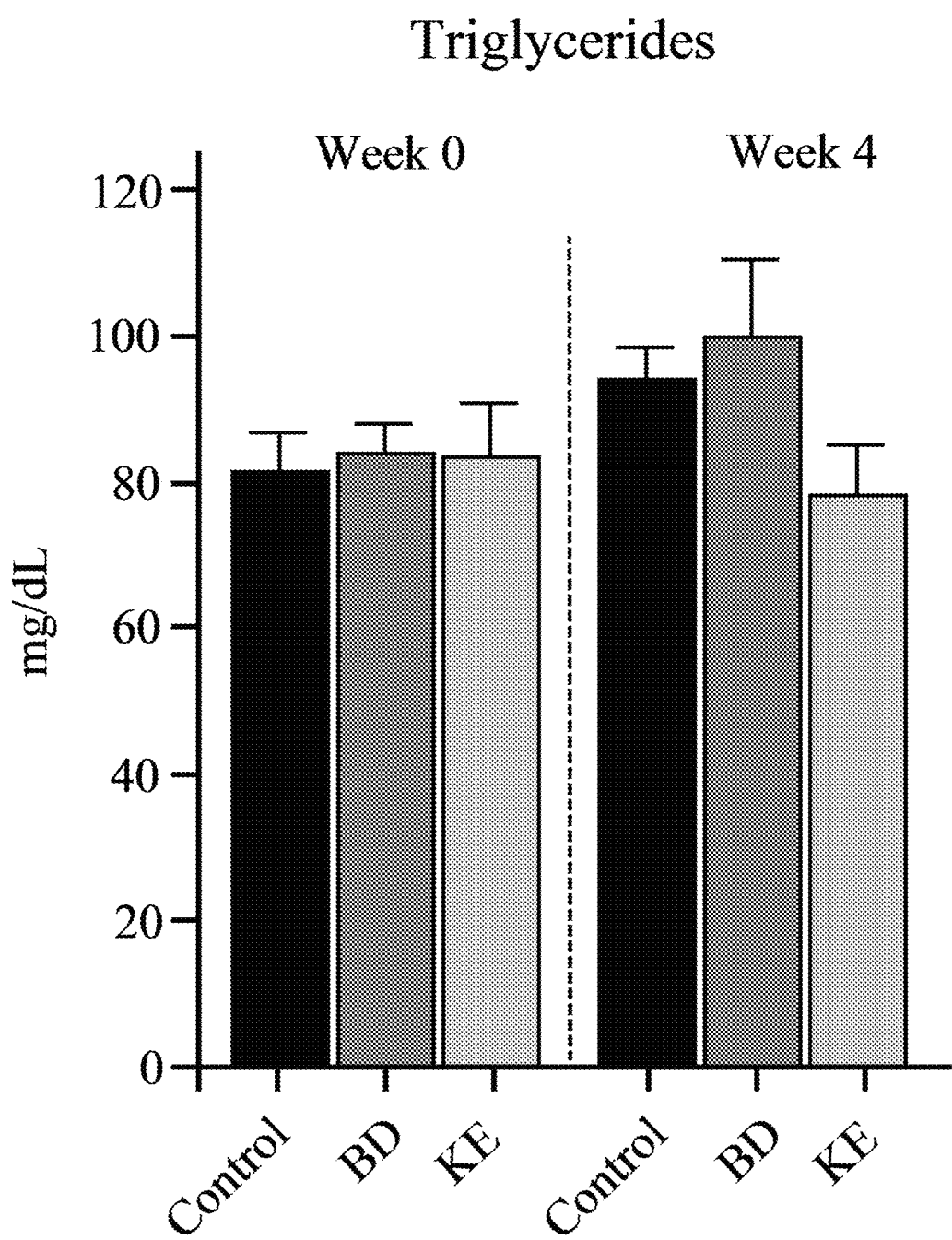
FIG. 12 is a graph showing ketone supplementation does not affect lipid profile. At week 0 and week 4 triglycerides were not significantly different from control in any of the test substances. Two-Way ANOVA with Dunnett's post hoc test, results considered significant if p<0.05. Error bars represent ±SEM.

Total Cholesterol and HDL, taken at week 0 and again at week 4, showed a reduction in all samples, including the control, as seen in FIGS. 10 and 11. Analysis showed the levels in all supplements were not significantly different from control after a 4-week chronic dosage of ketone supplements. Triglyceride levels were mildly elevated at week 4 in the control and Butanediol samples, with little change in levels of ketone ester sample, as seen in FIG. 12. However, none of the levels were significantly different from control after a 4-week chronic dosage of ketone supplements, indicating dietary ketone supplementation does not affect lipid profile.

Figure 13:
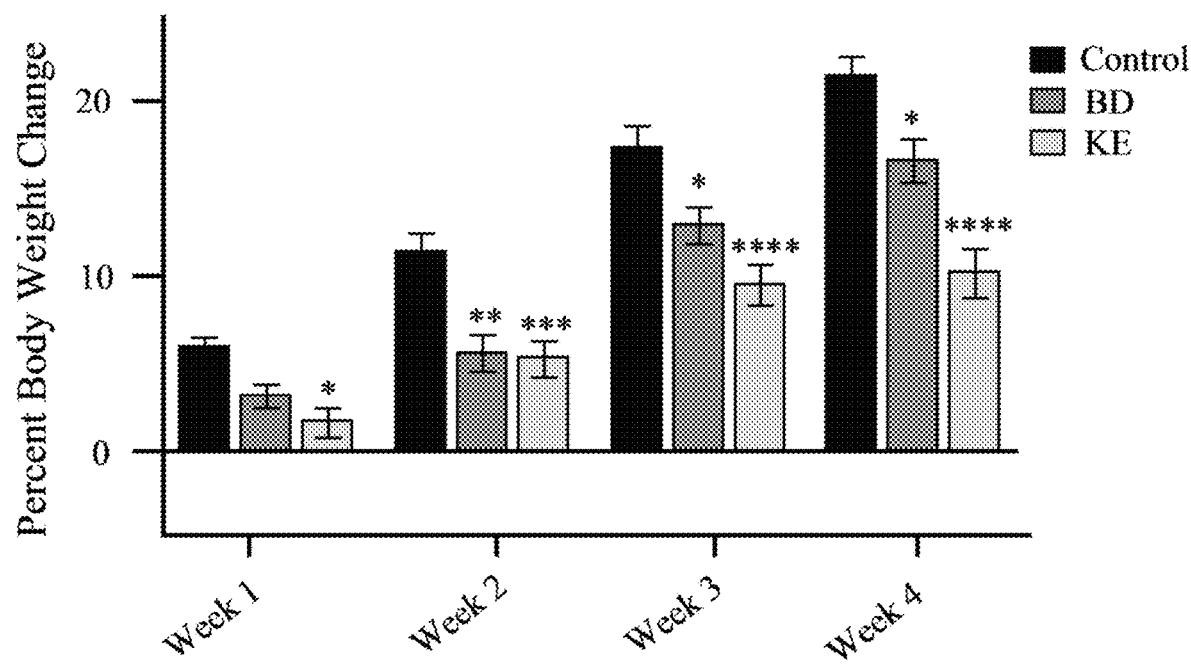
FIG. 13 is a graph showing the effects of ketone supplementation on change of body weight. *p<0.05;  p<0.01; * p<0.001; **** p<0.0001.

Animal weights were obtained weekly (Mittler Toledo SB16001 scales). Control rats steadily increased in weight over the 4 week study. BD treatment modestly decreased body weight increases, with differences in weight increases significant in weeks 2 through 4, as seen in FIG. 13. KE treatments further reduced weight gains compared to BD treatment, and were statistically significant at all test points.

Gavaging ketogenic agents resulted in lower blood glucose, reduced bodyweight and appetite suppression, which is much greater than seen with metformin. Butanediol is currently the most potent ketogenic agent for the price. Problem is the taste and at very high doses it can create mild intoxication or sedating effects. In early studies (agents added to food) it was thought that the effects were due to reducing palatability. Gavaging controlled for that and suggests the results are due to ketone-induced appetite suppression effects. Animals gavaged with either BD or KE gained significantly less weight compared to controls.

Example 2

Animals treated from Example 1 were sacrificed by $CO_2$ between 4-8 hours after gavage-treatment at the end of 4 weeks (28 days at the dose of 5-10 g/kg), which were determined to be peak ketone elevation. Brain, Lungs, Liver, Kidneys, Spleen and Heart were harvest and weighed using AWS-1000 1 kg portable digital scale (AWS, Charleston, S.C.). Organs were then either flash frozen in liquid nitrogen or preserved in paraformaldehyde for future analysis.

Figure 14:
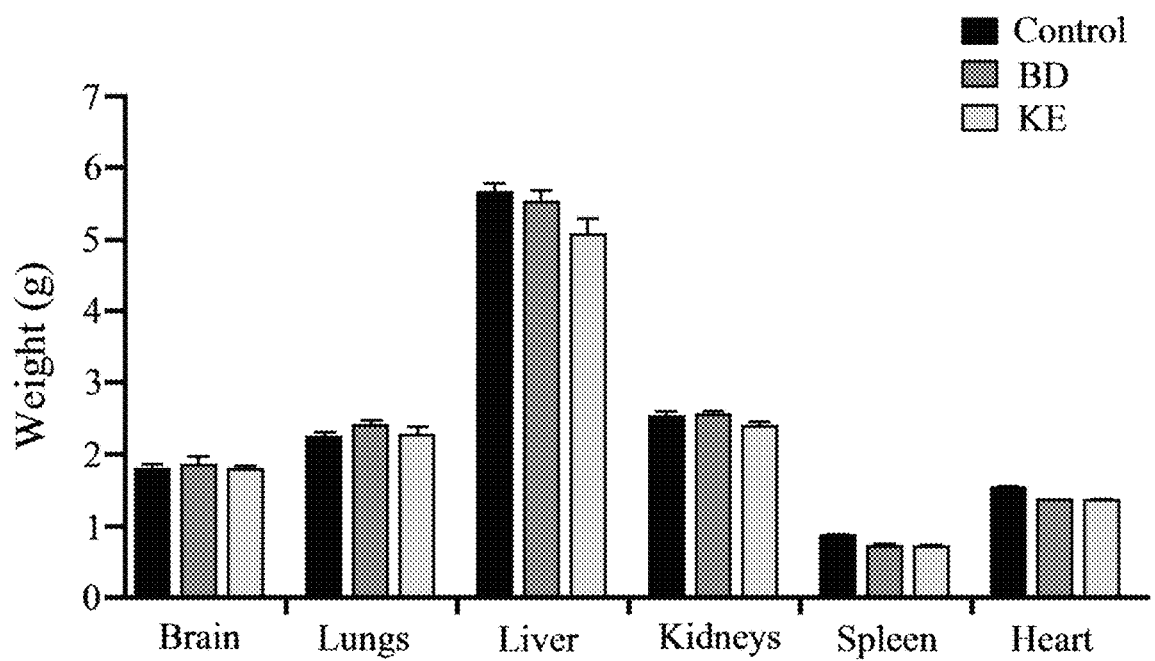
FIGS. 14(A) and (B) are graphs showing the effects of ketone supplementation on organ weights. (A) week 4 harvested organ weights and (B) week 4 harvested liver weights were significantly decreased in ketone ester supplement. There was not a significant change in liver weight with animals fed BD ketone supplement. Two-Way ANOVA with Dunnett's post hoc test, results considered significant if p<0.05. Error bars represent ±SEM. ** p<0.01.
Figure 14:
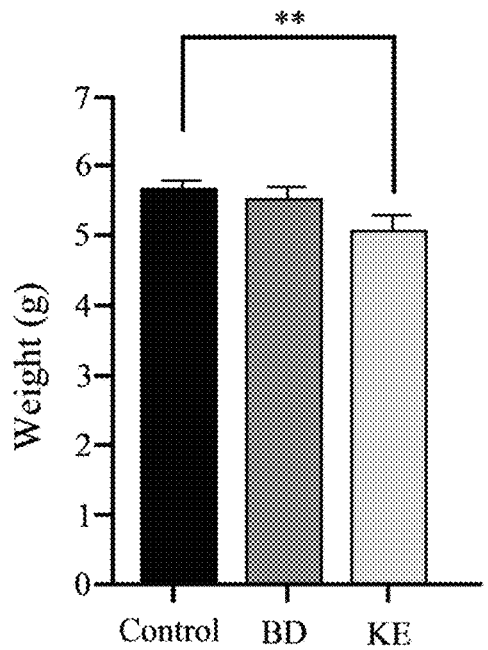

KE ketone supplements significantly decreased the weight of the liver in the rats. BD supplemented animals showed no significant change in non-liver organ weight, as seen in FIG. 14(A). However, KE treatment did result in a statistically significant reduction in liver weight, as seen in FIG. 14(B).

Livers from rats administered maximum tolerable dose of ketone supplementation were assessed via histology. The livers from rats treated 4-weeks with ketone supplementation appeared normal in color, size and texture in all groups upon harvesting. The livers were sectioned for histology and stained with Hematoxylin and Eosin (H&E stain), and analyzed by a trained pathologist to assess histopathological changes, including changes in liver cytoarchitecture, presence of steatosis, steatofibrosis, cell nuclei density, capillary density, presence of red blood cells (RBCs) and signs of inflammatory processes (e.g. macrophages).

TABLE 1

Statistical analysis of the binary relationship between ketone levels and glucose levels in KE and BD treatments.

| Compound | Week 0 | Week 1 | Week 2 | Week 3 | Week 4 |
| --- | --- | --- | --- | --- | --- |
| BD | $r^2 = 0.07855$<br>$p = 0.2600$* | $r^2 = 0.03847$<br>$p = 0.4354$* | $r^2 = 0.007530$<br>$p = 0.7321$* | $r^2 = 0.001469$<br>$p = 0.8839$* | $r^2 = 0.1005$<br>$p = 0.2150$* |
| KE | $r^2 = 0.1593$<br>$p = 0.1008$* | $r^2 = 0.03155$<br>$p = 0.4807$* | $r^2 = 0.1356$<br>$p = 0.1327$* | $r^2 = 0.4096$<br>$p = 0.0057$ | $r^2 = 0.2381$<br>$p = 0.0469$ |

*Results failed to reach statistical significance based on $p < 0.05$.

The representative images are liver sections of Sprague-Dawley that were gavaged daily with water; 1,3-butanediol (BD); Ketone Ester (KE);) for 28 days at the maximum tolerable dose (5-10 g/kg). There was a trend for greater number of RBCs and capillaries in BD- and KE-treated rats compared to control, which was most prevalent in the 1,3-butanediol group (data not shown). Fat deposits were evident in upon BE or KE treatment, with 1,3-butanediol treatment group showing the most prevalence of fat deposition. It should be noted that 1,3-butanediol has alcohol-like properties and requires hepatocytes to enzymatically metabolize the di-alcohol through cytosolic alcohol dehydrogenase and the induction of cytochrome p450 enzymes for conversion to βHB. The processes are associated with an increase in liver metabolism and blood flow, possibly resulting in greater number of RBCs and capillaries. There was also a modest, but statistically significant increase in hepatocyte cell nuclei, seen in Table 2, although no indications of liver damage, inflammation, fibrosis or presence of Mallory-Denk bodies were observed.

TABLE 2

The effect of ketone supplementation on hepatocyte nucleus number (based on minimum 5 images/animal, 5 animals/group). unpaired t-test; results considered significant if $p < 0.05$.

|  | Control | BD | KE |
| --- | --- | --- | --- |
| average | 95.36 | 93.56 | 107.80[a] |
| minimum | 79 | 70 | 83 |
| maximum | 123 | 120 | 141 |
| standard deviation | 10.01 | 12.97 | 16.00 |
| significance |  | 0.585 | 0.002 |

[a]statistically significant results.

Example 3

Ketones, beta-hydroxybutyrate (βHB) and acetoacetate (AcAc), are derived from acetyl-CoA generated from the oxidation of fatty acids in the liver. In extrahepatic tissues, they are converted back to acetyl-CoA where they serve as important fuel sources—especially in the heart and skeletal muscle. Most tissues in mature animals, under nutrient replete conditions, do not use ketones but can adapt to their use during starvation or prolonged exercise when glycogen stores become depleted. The underlying hypothesis behind the use of ketogenic agents for induction of nutritional ketosis is that ketones are a metabolic substrate that can be exploited through the oral administration of specific forms of supplementation. This global metabolic profiling study was conducted to examine the systemic and brain metabolic responses of healthy rats subjected to two different diets capable of inducing nutritional ketosis.

Rats were treated as described in Example 1, and brain and serum samples were extracted and prepared for analysis using a standard solvent extraction method (Metabolon Inc., Durham, N.C.) at 28 days after initiation of treatment. The extracted samples were split into equal parts for analysis on the GC/MS and LC/MS/MS platforms. Instrument variability was determined by calculating the median relative standard deviation (RSD) for the internal standards that were added to each sample prior to injection into the mass spectrometers.

Comparison of the biochemical profiles of serum and hippocampal samples collected from Sprague-Dawley rats fed a control diet (control) or a ketone ester diet (KE; BDAcAC$_2$) revealed several key metabolic differences. A total of 388 and 290 compounds were identified in serum and hippocampus samples, respectively. Statistical tests revealed a wide range of changes in serum among all diet groups whereas the number of statistically significant changes in the hippocampus was more limited. The less robust changes in the hippocampal tissue may have been due to the time frame needed to dissect the hippocampal tissue from the brain prior to flash freezing (2-4 minutes). Random Forest (RF) is a supervised classification technique reporting on the consensus of a large number of decision trees. In this study, the serum and hippocampus profiles of animals subjected to different dietary treatments were classified in order to: 1) assess the capacity to distinguish between dietary treatment on the basis of global metabolic profiles and 2) identify biochemicals important to the classification. A classification accuracy of 33% is expected by random chance when comparing three groups. For this study, classification of serum and hippocampus samples was 100% and 83% accurate, respectively, in correctly categorizing samples into their proper groups. This suggests that each ketogenic dietary treatment produced a distinct metabolic phenotype that was influenced by the specific properties of the ketone supplement. In serum, the biochemical key to classifying the groups included biomarkers related to ketones, energy metabolites, medium-chain fatty acids, and ketones were key factors for hippocampal group classification.

Figure 15:
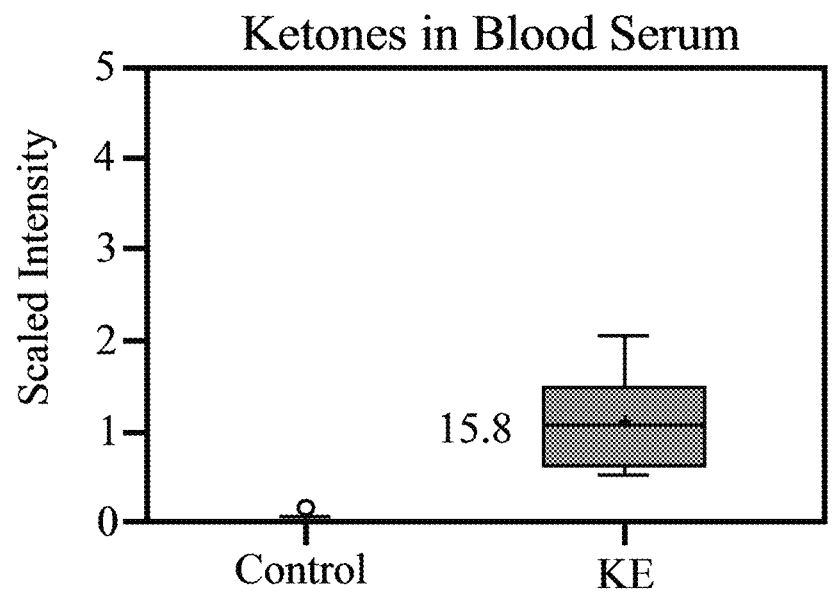
FIG. 15 is a graph showing levels of ketone in blood serum after 28-day KE treatment, n=8. Samples were equally split and analyzed on GC/MS and LC/MS/MS platforms. Error bars represent ±SEM.
Figure 16:
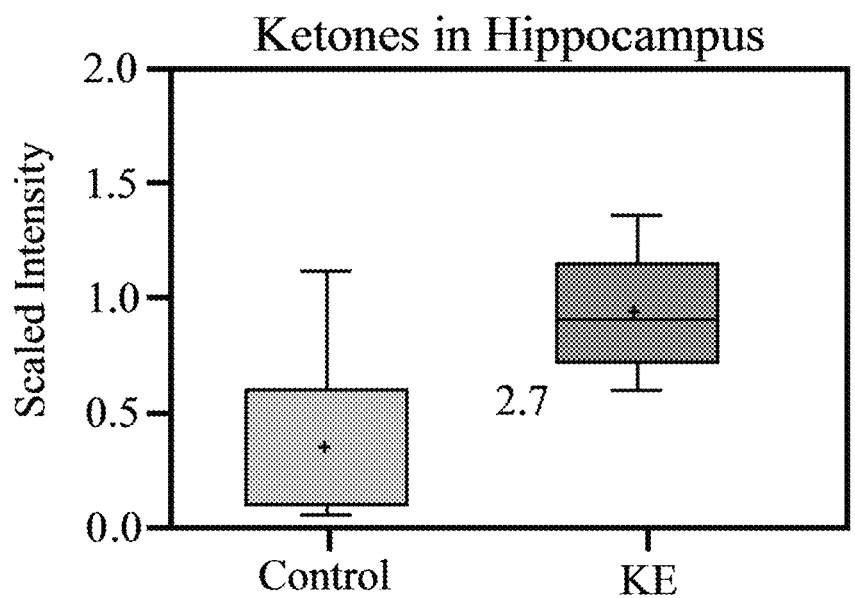
FIG. 16 is a graph showing levels of ketone in the hippocampus after 28-day KE treatment, n=8. Samples were equally split and analyzed on GC/MS and LC/MS/MS platforms. Error bars represent ±SEM.
Figure 17:
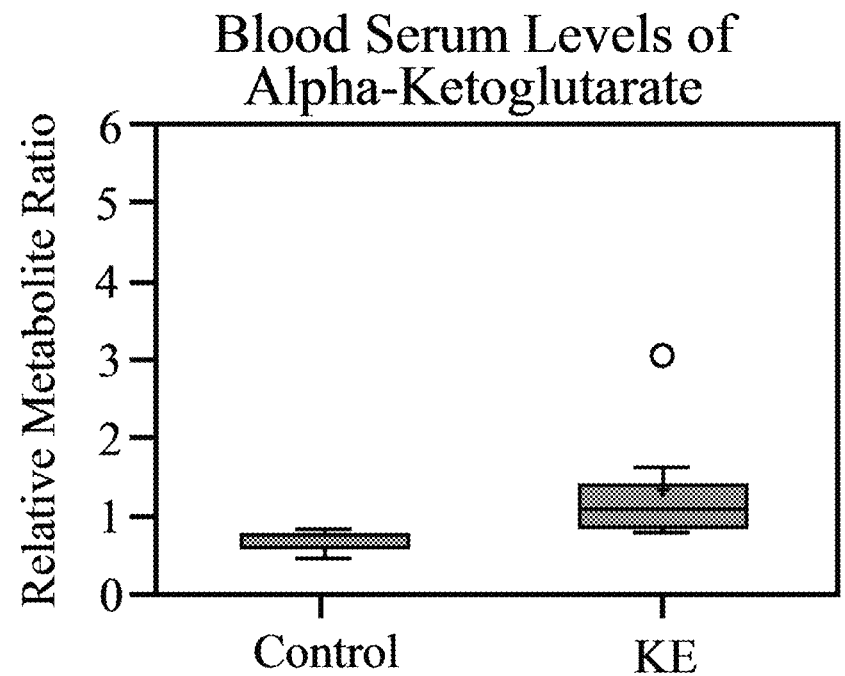
FIG. 17 is a graph showing levels of the Krebs cycle (TCA) intermediate alpha-ketoglutarate in blood serum after 28-day KE treatment, indicating an anaplerotic mechanism. Error bars represent ±SEM.
Figure 18:
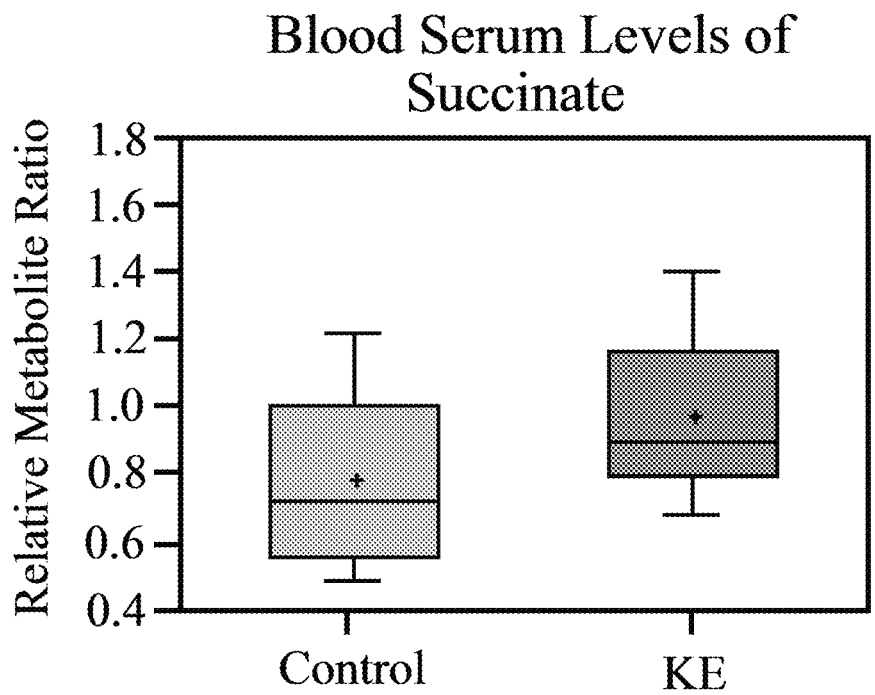
FIG. 18 is a graph showing levels of Krebs cycle (TCA) intermediate succinate in blood serum after 28-day KE treatment, indicating an anaplerotic mechanism. Error bars represent ±SEM.
Figure 19:
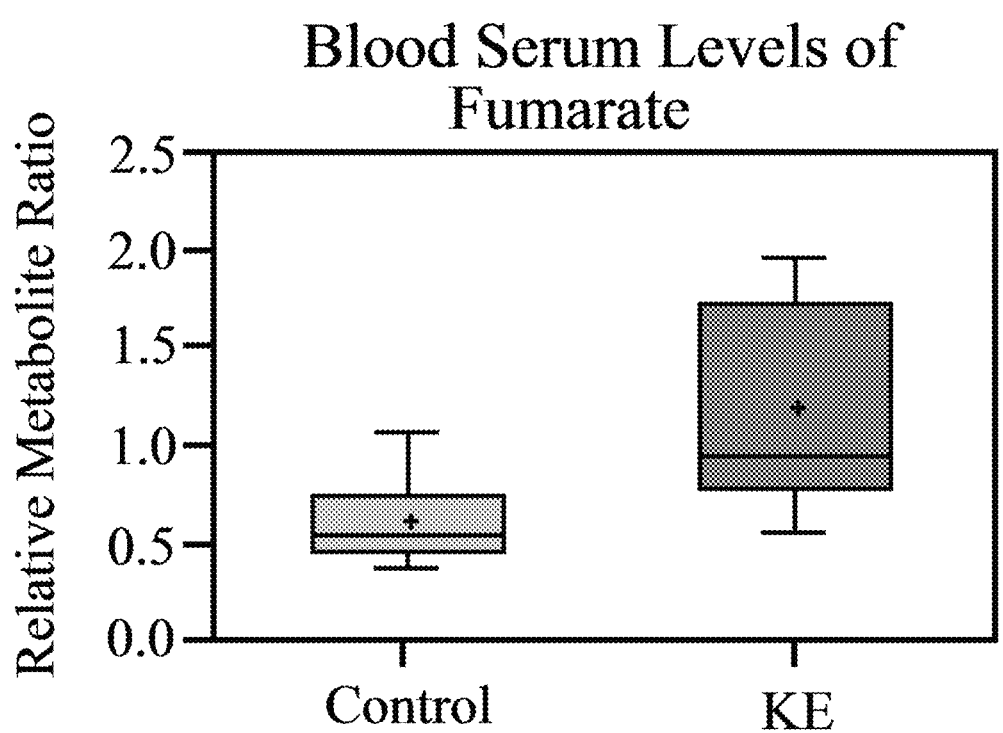
FIG. 19 is a graph showing levels of Krebs cycle (TCA) intermediate fumarate in blood serum after 28-day KE treatment, indicating an anaplerotic mechanism. Error bars represent ±SEM.
Figure 20:
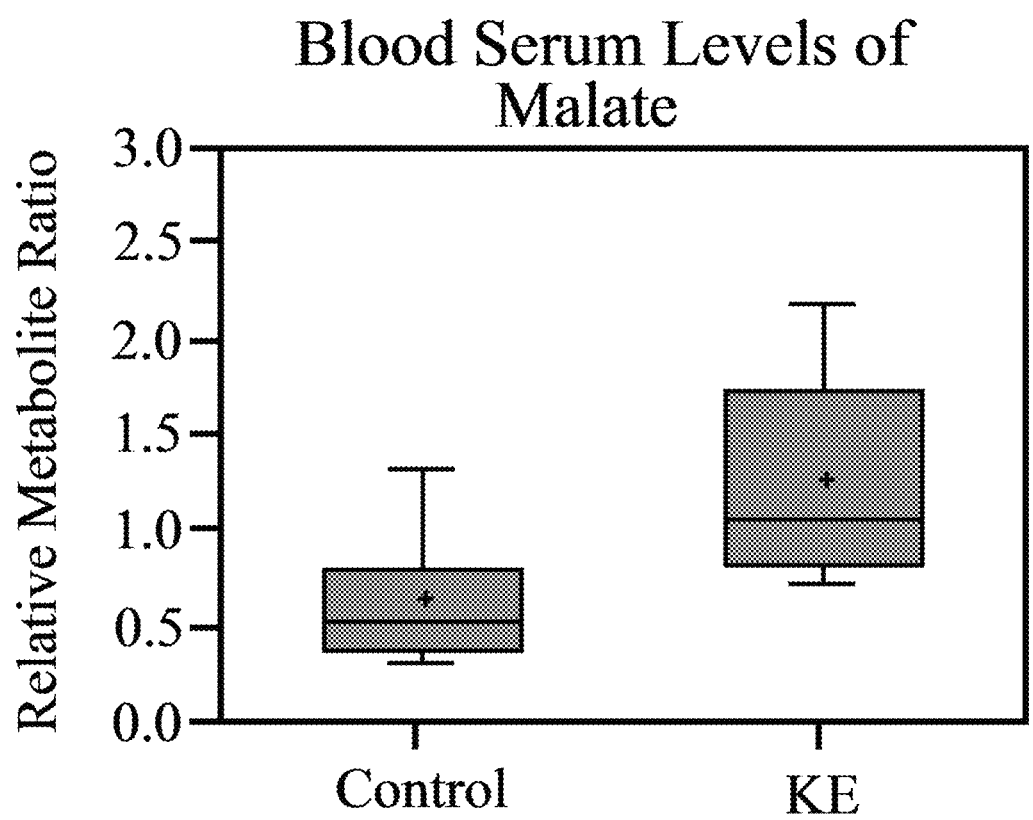
FIG. 20 is a graph showing levels of Krebs cycle (TCA) intermediate malate in blood serum after 28-day KE treatment, indicating an anaplerotic mechanism. Error bars represent ±SEM.
Figure 21:
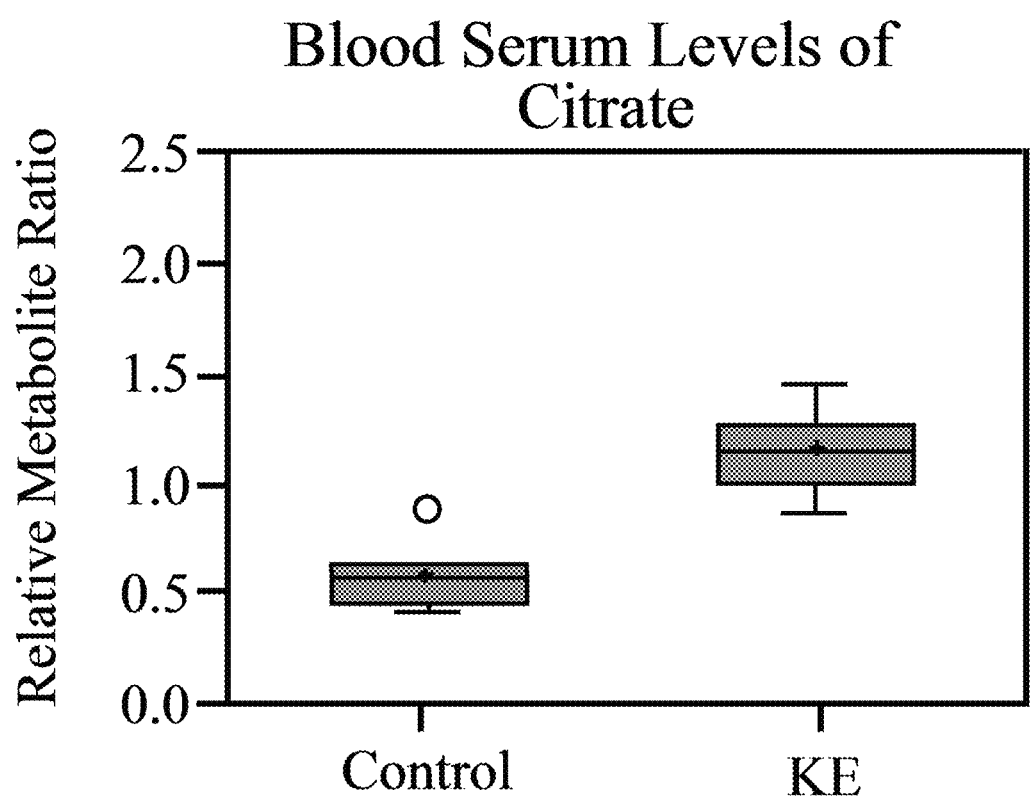
FIG. 21 is a graph showing levels of Krebs cycle (TCA) intermediate citrate in blood serum after 28-day KE treatment, indicating an anaplerotic mechanism. Error bars represent ±SEM.

Metabolomic analysis showed a significant elevation, with respect to controls, of serum ketone levels (>15 fold), seen in FIG. 15, and brain ketone levels (>2 fold), seen in FIG. 16, following administration of ketone esters (KE). In addition, and tricarboxylic acid cycle (TCA, a.k.a., Szent-Gyorgyi Krebs cycle) intermediates were significantly elevated following 28 days of ketone esters administration, as seen in FIGS. 17-21 and Table 3.

TABLE 3

The metabolite ratio relative to a standard diet (SD) alone.

| TCA intermediate | ketone ester (5 g/kg) |
| --- | --- |
| alpha-ketoglutarate | 1.98[a] |
| succinate | 1.25 |
| fumarate | 1.92[a] |
| malate | 2.03[a] |
| citrate | 1.99[a] |

[a]significant difference ($p \leq 0.05$) between the groups shown; metabolite ratio of $\geq 1.00$.

The significant boost in anaplerosis demonstrates elevated energy reserves and increased anabolic precursors for synthesis of other metabolic substrates and neurotransmitters, including adenosine, which has anticonvulsant and neuroprotective properties. In addition to elevated TCA cycle intermediates was a significant elevation of carnosine and anserine, which play a major role in preserving antioxidant status and reducing fatigue during exercise. These data provide evidence that ketone supplementation produces a metabolic profile that is consistent with increased metabolic resilience and antioxidant neuroprotection against oxidative and metabolic stress associated with CNS-OT.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of the method of improving wound healing, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of suppressing hunger in a human patient in need thereof comprising: administering a therapeutically effective amount of a composition comprising a ketogenic agent to elevate one or more ketone bodies for at least four (4) hours and suppress hunger in the human patient;
   wherein the ketogenic agent is R,S-1,3-butanediol acetoacetate monoester; R,S-1,3-butanediol diacetoacetate ester; or a combination thereof;
   wherein administration of the composition induces ketosis in the human patient, and
   wherein the human patient consumes an average of greater than 50 g of carbohydrate per day.

2. The method of claim 1, wherein the ketogenic agent is R,S-1,3-butanediol diacetoacetate ester.

3. The method of claim 1, wherein the ketogenic agent is administered at between 5 g/kg and 10 g/kg, or wherein each ketogenic agent is administered at between 5 g/kg and 10 g/kg.

4. The method of claim 3, wherein the ketogenic agent is administered at 5 g/kg, 6 g/kg, 7 g/kg, 8 g/kg, 9 g/kg, or 10 g/kg.

5. The method of claim 3, wherein each ketogenic agent is administered at 5 g/kg, 6 g/kg, 7 g/kg, 8 g/kg, 9 g/kg, or 10 g/kg.

6. The method of claim 1, wherein the ketogenic agent is administered between about 2 g/day and about 50 g/day, or wherein each ketogenic agent is administered between about 2 g/day and about 50 g/day.

7. The method of claim 1, wherein the one or more ketone bodies in the human patient is present in a concentration of 1.1 mM/L or greater.

8. The method of claim 1, wherein the ketone supplement is administered chronically.

9. The method of claim 1, wherein the ketogenic agent is administered between about 2 g/day and about 15 g/day.

* * * * *